US011241510B2

(12) United States Patent
Annapragada et al.

(10) Patent No.: US 11,241,510 B2
(45) Date of Patent: Feb. 8, 2022

(54) HYDROPHILIC FLUORINATED MOLECULES FOR LIPOSOMAL 19F MRI PROBES WITH UNIQUE MR SIGNATURES

(71) Applicant: TEXAS CHILDREN'S HOSPITAL, Houston, TX (US)

(72) Inventors: Ananth Annapragada, Houston, TX (US); Eric A. Tanifum, Houston, TX (US)

(73) Assignee: TEXAS CHILDREN'S HOSPITAL, Houston, TX (US)

( * ) Notice: Subject to any disclaimer, the term of this patent is extended or adjusted under 35 U.S.C. 154(b) by 0 days.

(21) Appl. No.: 15/827,782

(22) Filed: Nov. 30, 2017

(65) Prior Publication Data

US 2018/0154025 A1 Jun. 7, 2018

Related U.S. Application Data

(60) Provisional application No. 62/428,434, filed on Nov. 30, 2016.

(51) Int. Cl.
| | |
|---|---|
| A61K 51/00 | (2006.01) |
| A61M 36/14 | (2006.01) |
| A61K 51/04 | (2006.01) |
| A61K 49/10 | (2006.01) |
| A61K 49/12 | (2006.01) |
| A61K 49/18 | (2006.01) |
| A61K 51/12 | (2006.01) |

(52) U.S. Cl.
CPC .......... *A61K 51/0453* (2013.01); *A61K 49/10* (2013.01); *A61K 49/124* (2013.01); *A61K 49/1812* (2013.01); *A61K 51/0491* (2013.01); *A61K 51/1234* (2013.01)

(58) Field of Classification Search
CPC ............ A61K 51/0453; A61K 51/0491; A61K 51/1234
USPC ....................................................... 424/1.73
See application file for complete search history.

(56) References Cited

U.S. PATENT DOCUMENTS

| | | | |
|---|---|---|---|
| 2003/0236407 A1 | 12/2003 | Schafer et al. | |
| 2011/0123457 A1 | 5/2011 | Yu | |
| 2012/0258044 A1 | 10/2012 | Annapragada et al. | |
| 2013/0108551 A1 | 5/2013 | Langereis et al. | |
| 2016/0101197 A1 | 4/2016 | Annapragada et al. | |

FOREIGN PATENT DOCUMENTS

| | | | | |
|---|---|---|---|---|
| EP | 2148881 | | 2/2010 | |
| GB | 1204862 | A * | 9/1970 | ......... A61K 49/0442 |
| JP | 11217385 | A * | 8/1999 | |
| WO | WO 2008/132433 | | 11/2008 | |

OTHER PUBLICATIONS

Weng et al. Chin. J. Chem. 1998, 28-33.*
Achilefu et al., "Introduction to Concepts and Strategies for Molecular Imaging," *Chemical Reviews*, 110:2575-2578, (2010).
Allen et al., "Liposomal drug delivery systems: from concept to clinical applications," *Advanced Drug Delivery Reviews*, 65:36-48, (2013).
Bentzen et al., "Molecular imaging-based dose painting: A novel paradigm for radiation therapy prescription," *Semin Radiat Oncol.*, 21:101-110, (2011).
Chen et al., "Quantitative Magnetic Resonance Fluorine Imaging: Today and tomorrow," *Wiley Interdisciplinary Review: Nanomedicine and Nanobiotechnology*, 2:431-440, (2010).
Debbage et al., "Molecular imaging with nanoparticles: giant roles for dwarf actors," *Histochemistry and Cell Biology*, 130:845-875, (2008).
International Search Report and Written Opinion issued in International Application No. PCT/IB17/57555, dated Feb. 22, 2018.
Janjic et al., "Self-delivering Nanoemulsions for Dual Fluorine-19 MRI and Fluorescence Detection," *J. Am. Chem. Soc.*, 130(9):2832-2841, (2008).
Jeraj et al., "Molecular Imaging to Plan Radiotherapy and Evaluate Its Efficacy," *J. Nucl. Med.*, 56:1752-1765, (2015).
Joshi et al., "Radiation dosimetry of florbetapir F 18," *EJNMMI Research*, 4:4, (2014).
Kenny et al., "A bisphosphonate for $^{19}$F-magnetic resonance imaging," *Journal of Fluorine Chemistry*, 184:58-64, (2016).
Kimura et al., "19F Magnetic resonance imaging of perfluorooctanoic acid encapsulated in liposome for biodistribution measurement." *Magnetic Resonance Imaging*, 22:855, (2004).
Kolb et al., "Click Chemistry: Diverse Chemical Function From a Few Good Reaction," *Angewandte Chemie International Edition*, 40:2004, (2001).
Lanza et al., "Targeted Antiproliferative Drug Delivery to Vascular Smooth Muscle Cells with a Magnetic Resonance imaging Nanoparticle Contrast Agent," *Circulation*, 106:2842-2847, (2002).
Lu et al., "Personalized medicine and human genetic diversity," *Cold Spring Harb Perspect Med*, 4:a008581, (2014).
Marusyk et al., "Tumor heterogeneity: Causes and consequences," *Biochimica et Biophysica Acta (BBA)—Reviews on Cancer*, 1805:105, (2010).
Matsuoka et al., "Micellization of fluorinated amphiphiles," *Current Opinion in Colloid & Interface Science*, 8:227, (2003).
Partlow et al., "19F magnetic resonance imaging for stem/progenitor cell tracking with multiple unique perfluorocarbon nanobeacons," *The FASEB Journal*, 21:1647-1654, (2007).

(Continued)

*Primary Examiner* — Michael G. Hartley
*Assistant Examiner* — Sean R Donohue
(74) *Attorney, Agent, or Firm* — Norton Rose Fulbright US LLP

(57) ABSTRACT

Readily available hydrophilic and small organofluorine moieties were condensed via "click chemistry" to generate nonionic hydrophilic fluorinated molecules with unique $^{19}$F MR signatures. These were used to fabricate stable liposome formulations for imaging various tissue types. This approach was tailored to exploit the broad spectrum of organic $^{19}$F molecular species and to generate probes with distinct $^{19}$F MRI signatures for simultaneous assessment of multiple molecular targets within the same target volume.

10 Claims, 13 Drawing Sheets

(56) References Cited

OTHER PUBLICATIONS

Ramachandran et al., "Fluorine Electron Double Resonance Imaging for $^{19}$F MRI in Low Magnetic Fields," *Magnetic Resonance in Medicine*, 48:523-529, (2002).

Ruiz-Cabello et al., "Fluorine (19F) MRS and MRI in biomedicine," *NMR in Biomedicine*, 24:114, (2011).

Srinivas et al., "(19)F MRI for quantitative in vivo cell tracking," *Trend in Biotechnology*, 28-363-70, (2010).

Srinivas et al., "Fluorine-19 MRI for visualization and quantification of cell migration in a diabetes model," *Magnetic* 58:725-734, (2007).

Tirotta et al., "19 F Magnetic Resonance Imaging (MRI): From Design of Materials to Clinical Applications," *Chemical Reviews*, 115:1106, (2015).

Tirotta et al., "A Superfluroinated Molecular Probe for Highly Sensitive in Vivo$^{19}$F-MRI," *M. Am. Chem. Soc.*, 136(24): 8524-8527, (2014).

Wang et al., "Activatable Dendritic $^{19}$F Probes for Enzyme Detection," *ACS Macro Letters*, 4:422-425, (2015).

Li et al. "Fluorous synthesis of mono-dispersed poly(ethylene glycols)" *Tetrahedron Letters* 2014, 55(13), 2110-2113.

Li et al., "Synthesis of gemini surfactants with twelve symmetric fluorine atoms and one singlet $^{19}$F MR signal as novel $^{19}$F MRI agents" *Tetrahedron* 2013, 69(46), 9586-9590.

Lim et al., "A facile one-pot synthesis of novel amphiphilic perfluoroalkyl ester functionalized γ-cyclodextrin and complex formation with anionic surfactants" *Journal of Fluorine Chemistry* 2006, 127(6), 730-735.

Millett et al., "Fluorine-19 nuclear magnetic resonance study of the binding of trifluoroacetylglucosamine oligomers to lysozyme" *Biochemistry* 1972, 11(9), 1639-1643.

Partial European Search Report issued in Corresponding European Application No. 17877351.1, dated Jun. 8, 2020.

Office Action Issued in Corresponding Chinese Patent Application No. 2017800735993, dated Jan. 15, 2021.

Search Report Issued in Corresponding Chinese Patent Application No. 2017800735993, dated Jan. 15, 2021.

Examination Report issued in Corresponding issued in European Application No. 17877351.1, dated Jun. 30, 2021.

Pandey et al., "Fluorinated photosensitizers: synthesis, photophysical, electrochemical, intracellular localization, in vitro photosensitizing efficacy and determination of tumor-uptake by 19F in vivo NMR spectroscopy" *Tetrahedron* 2003, 59, 10059-10073.

Tanifum et al., "Hydrophilic fluorinated molecules for spectral $^{19}$F MRI" *Scientific Reports* 2018, 8(1):2889, 8 pages.

* cited by examiner

HYDROPHILIC FLUORINATED MOLECULES FOR LIPOSOMAL 19F MRI PROBES WITH UNIQUE MR SIGNATURES

CROSS-REFERENCE TO RELATED APPLICATIONS

This application claims the benefit of U.S. Provisional Application No. 62/428,434, filed Nov. 30, 2016, which is incorporated herein in its entirety.

BACKGROUND OF THE INVENTION

A. Field of the Invention

The invention generally relates to the fields of radiology and organic chemistry. In particular, the invention concerns hydrophilic, non-toxic Fluorine-19 ($^{19}$F) contrast agents for $^{19}$F MRI.

B. Description of Related Art

Recent technological advances in molecular pathology have revolutionized the understanding of several diseases at the cellular and molecular levels. This knowledge enables improved diagnoses, allows treatment plans to be directed to specific targets, and translates to better treatment outcomes [1-3]. Equivalent technologies for noninvasive in vivo evaluation of disease activity and therapeutic efficacy will enable the development of novel diagnostic and therapeutic techniques. To this end, molecular imaging techniques including positron emission tomography (PET), single-photon emission computed tomography (SPECT), optical imaging with fluorescent probes and several magnetic resonance imaging/spectroscopy (MRI/MRS) platforms are in development to assess molecular targets and metabolic processes in vivo [4].

Today, nuclear molecular imaging methods (PET and SPECT) dominate clinical settings, but result in significant radiation exposure. A single PET scan may results in up to 7 millisieverts (mSv) of radiation exposure [5], which is equivalent to about 70 chest x-rays. Repeated exposure of patients to positron emission reagents is therefore not recommended. Optical molecular imaging techniques are limited by imaging depth. These techniques find use in small animal studies, and are less useful in larger animals. A versatile, non-radioactive molecular imaging probe with no tissue depth limitations is therefore highly desirable.

When administered in vivo, the ideal molecular imaging probe should detect, localize and report on a process/activity within a cell or tissue, with high sensitivity and specificity. The biocompatibility of liposomes, their ability to carry diverse payloads, and the ease with which they can be ligand-targeted to specific molecular targets, make them an excellent nanoparticle platform for molecular imaging [6, 7]. In addition, sensitivity can easily be maximized by optimizing the payload capacity per particle.

$^{19}$F MRI is emerging as a molecular imaging modality with broad applications in biomedicine for several reasons. Fluorine's gyromagnetic ratio is very close to that of the proton ($^1$H), so current $^1$H MRI hardware requires minimal changes to acquire $^{19}$F-based images. Further, there is no MRI-detectable endogenous $^{19}$F, leading to images with very high signal-to-noise ratios (SNR). There is a linear relationship between contrast agent concentration and signal intensity, which allows direct and unambiguous quantification of disease activity [8, 9]. Most importantly, organofluorine molecules have a broad chemical shift range of >350 ppm. Current receiver bandwidth suggests a peak separation of ~12 ppm to individually image multiple $^{19}$F species without introducing chemical shift artifacts. This allows the concurrent use of as many as 30 $^{19}$F probes with unique MRI signatures.

$^{19}$F MRI is limited by sensitivity, and a large number of $^{19}$F atoms must be present in each voxel of target volume to enable high conspicuity. A number of nanoparticle formulations have been suggested to address this limitation. These include perfluorocarbons (PFCs), perfluoropolyethers (PFPEs), dendrimers, fluorinated amphiphiles and other hyperfluorinated molecules such as PERFECTA [10]. To date, PFCs and PFPEs dominate the preclinical/clinical space, but they have several drawbacks, including low aqueous solubility (limiting formulation to water emulsions requiring surfactants), limited shelf stability [11], and magnetically diverse fluorine atoms (resulting in chemical shift artifacts and diffuse images) [12].

SUMMARY OF THE INVENTION

A solution to the aforementioned problems with molecular imaging techniques has been discovered. In some embodiments, the solution resides in highly hydrophilic, nonionic, fluorinated probes bearing a plurality of magnetically equivalent $^{19}$F atoms. Such probes are able to form stable aqueous formulations using a liposome nanoparticle. In some embodiments, multiple probes having distinct $^{19}$F MRI signatures can be employed for simultaneous assessment of multiple molecular targets within the same target volume, without any chemical shift artifacts or interference with the signal of the inhalable anesthesia isoflurane.

Some aspects of the disclosure are directed towards nonionic $^{19}$F-MR contrast molecules comprising at least two fluorine atoms, at least one 1,2,3-triazole moiety, and at least one vicinal diol group. In some aspects, the at least two fluorine atoms are magnetically equivalent. In some embodiments, the contrast molecule has at least one plane of symmetry. In further embodiments, the contrast molecule has at least one axis of symmetry.

Some aspects of the disclosure are directed to nonionic $^{19}$F-MR contrast molecules having the formula X—(R)$_n$, wherein X comprises at least two magnetically equivalent fluorine atoms, wherein R is a nonionic, hydrophilic moiety comprising at least two alkyl alcohol moieties, and wherein n is an integer equal to or greater than 1. In some aspects the fluorine atoms are $^{19}$F. In some aspects, n is 1, 2, 3, 4, 5, 6, 7, 8, 9, 10, 11, or 12 or greater. In some aspects, R comprises a vicinal diol moiety. In some aspects, the $^{19}$F-MR contrast molecules described herein comprise a hexose moiety. In some embodiments, the contrast molecule has at least one plane of symmetry. In further embodiments, the contrast molecule has at least one axis of symmetry. In some embodiments, X is selected from the group consisting of:

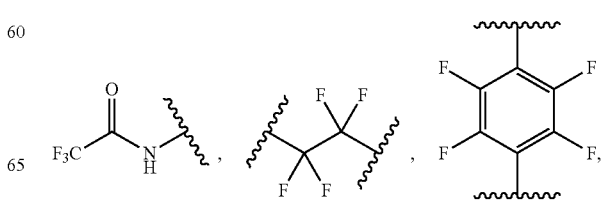

-continued

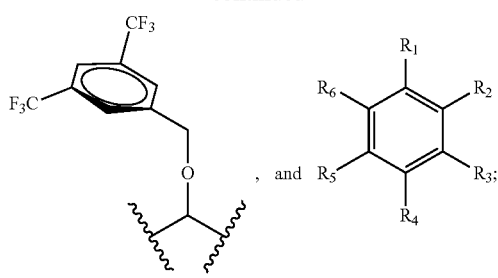, and 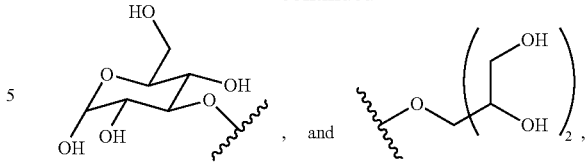

wherein $R_1$-$R_6$ are each independently H or —$(CH_2O)_a$ $(CH_2)_b(CF_2)_c(CH_2)_d$—; at least one of $R_1$-$R_6$ is —$(CH_2O)_a$ $(CH_2)_b(CF_2)_c(CH_2)_d$—; a, b, and d are each independently an integer from 0 to 5; and c is an integer from 1 to 5.

In some embodiments, R is selected from the group consisting of

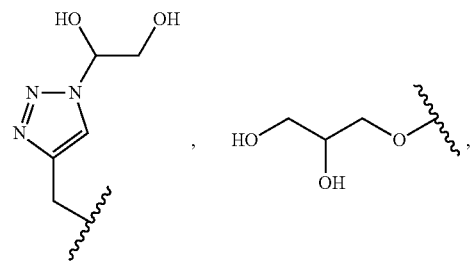,

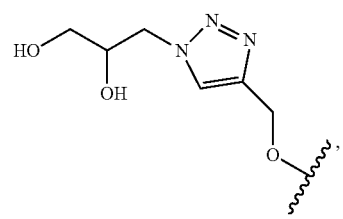,

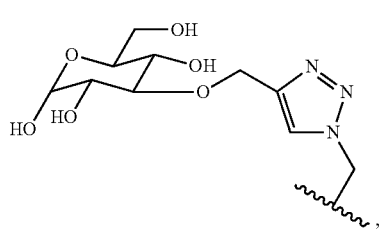,

-continued

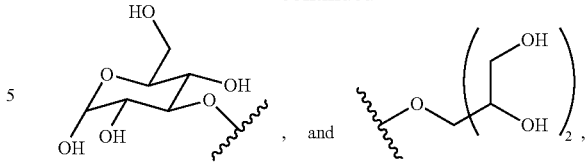

In some aspects, R comprises a saccharide moiety. In certain aspects, the saccharide moiety is a hexose moiety. In particular aspects, the hexose moiety is a glucose moiety.

Some aspects of the disclosure are directed towards nonionic $^{19}$F-MR contrast molecules comprising at least a saccharide moiety. In certain aspects, the saccharide moiety is a hexose moiety. In particular aspects, the hexose moiety is a glucose moiety.

In some embodiments, the $^{19}$F-MR contrast molecules disclosed herein are not dendrimeric, i.e., they are not repetitively branched. In some aspects, the $^{19}$F-MR contrast molecules disclosed herein have a molecular weight of less than 900 g/mole. In some embodiments, the $^{19}$F-MR contrast molecules disclosed herein are water soluble. In further embodiments, the $^{19}$F-MR contrast molecules disclosed herein are hydrophilic. The $^{19}$F-MR contrast molecules disclosed herein comprise polar functional groups which impart hydrophilic character on the molecules. The polar functional groups include but are not limited to amides; ethers; alcohols; polyols, for example, vicinal diols; saccharides, for example, glucose; and heterocycles, including 1,2,3-triazoles. In some embodiments, the $^{19}$F-MR contrast molecules disclosed herein have an n-octanol/water partition coefficient (log P) of less than −1. The n-octanol/water partition coefficient of a molecule is determined by dissolving the molecule in an immiscible mixture of n-octanol and water and measuring the respective equilibrium concentrations of the molecule in the n-octanol and water phases; the partition coefficient, log P, is calculated as the logarithm of [molecule]n-octanol divided by [molecule]$_{water}$. In some embodiments, the $^{19}$F-MR contrast molecules disclosed herein have a calculated n-octanol/water partition coefficient (C log P) of less than −1. In some aspects, each of the $^{19}$F-MR contrast molecules disclosed herein comprises a polar surface area that contributes to the molecule's hydrophilicity. In some embodiments, each of the $^{19}$F-MR contrast molecules disclosed herein comprises a minimum topological polar surface area. In some embodiments, the $^{19}$F-MR contrast molecules' minimum topological polar surface area is 80.

The $^{19}$F-MR contrast molecules disclosed herein include without limitation
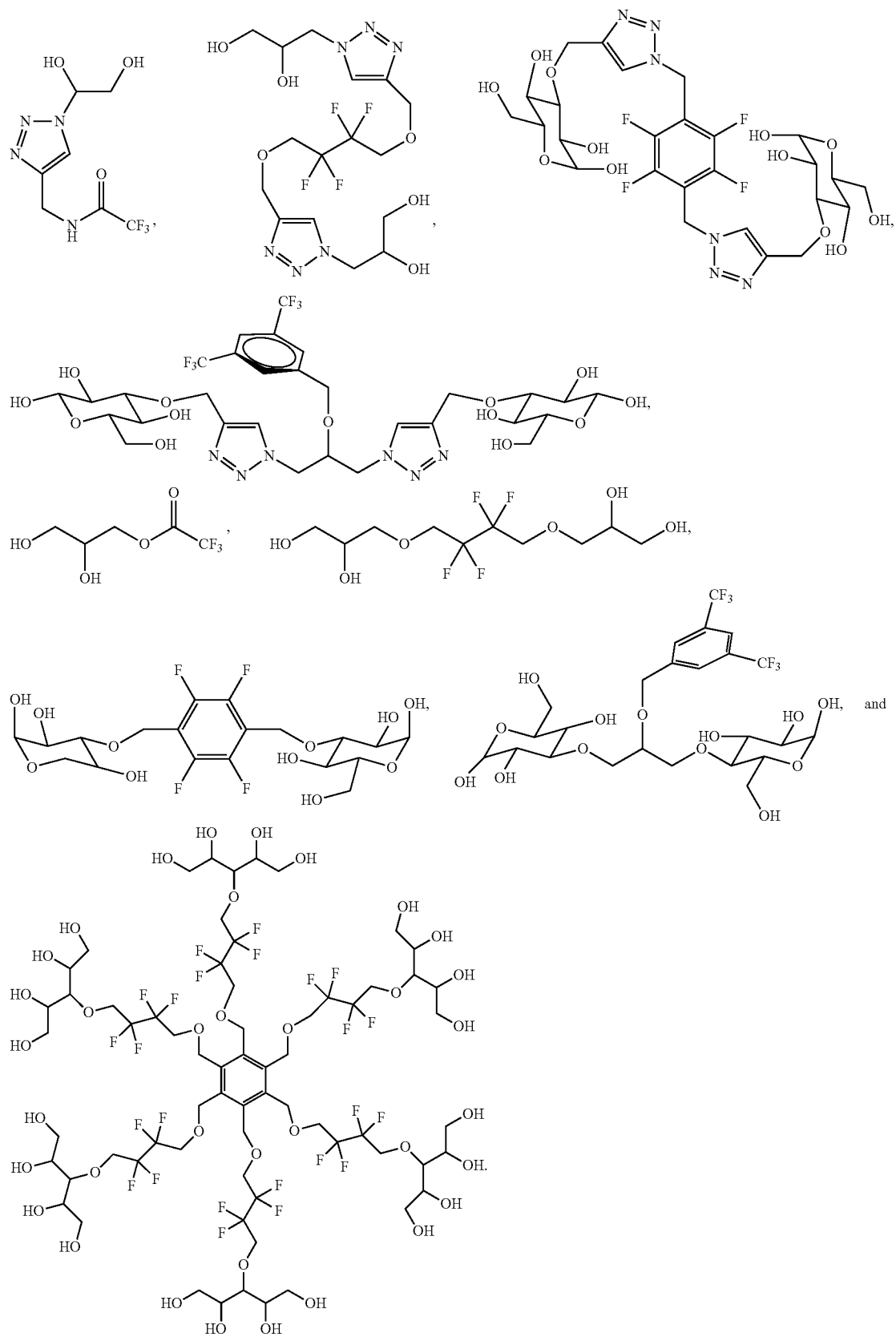

Some aspects of the disclosure are directed towards liposome compositions for the administration of one or more $^{19}$F-MR contrast molecules. In some embodiments, a liposome composition comprises a liposome and one or more $^{19}$F-MR contrast molecules. The liposome may comprise a unilaminar bilayer of at least one lipid. In some embodiments, the liposome is a multilamellar liposome. In some embodiments, each the one or more $^{19}$F-MR contrast molecules comprises at least two fluorine atoms, at least one 1,2,3-triazole moiety, and at least one vicinal diol group. The liposome composition may comprise any of the $^{19}$F-MR contrast molecules disclosed herein.

In some embodiments, the liposome lipid comprises one or more hydrocarbon chains and a polar head group. Liposome lipids may be selected from the lipid families that include glycerolipids, propylene glycol phospholipids, glycerophospholipids (phospholipids), sphingolipids, prenol lipids, sterol lipids, saccharolipids, and polyketides. A glycerolipid may be a mono-, di-, or tri-substituted glycerol. Exemplary glycerophospholipids include phosphatidyl cholines, phosphatidylethanolamines, phosphatidic acids, and phosphatidylinositols. Exemplary, non-limiting examples of liposome phospholipids include 1,2-didecanoyl-sn-glycero-3-phosphocholine, 1,2-dierucoyl-sn-glycero-3-phosphate, 1,2-dierucoyl-sn-glycero-3-phosphoethanolamine, 1,2-dierucoyl-sn-glycero-3-phosphocholine, 1,2-dilinoleoyl-sn-glycero-3-phosphocholine, 1,2-dilauroyl-sn-glycero-3-phosphate, 1,2-eilauroyl-sn-glycero-3-phosphocholine, 1,2-dilauroyl-sn-glycero-3-phosphoethanolamine, 1,2-eilauroyl-sn-glycero-3-phosphoserine, 1,2-dimyristoyl-sn-glycero-3-phosphate, 1,2-eimyristoyl-sn-glycero-3-phosphocholine, 1,2-dimyristoyl-sn-glycero-3-phosphoethanolamine, 1,2-eimyristoyl-sn-glycero-3-phosphoserine, 1,2-dioleoyl-sn-glycero-3-phosphate, 1,2-eioleoyl-sn-glycero-3-phosphocholine, 1,2-dioleoyl-sn-glycero-3-phosphoethanolamine, 1,2-eioleoyl-sn-glycero-3-phosphoserine, 1,2-dipalmitoyl-sn-glycero-3-phosphate, 1,2-eipalmitoyl-sn-glycero-3-phosphocholine, 1,2-dipalmitoyl-sn-glycero-3-phosphoethanolamine, 1,2-eipalmitoyl-sn-glycero-3-phosphoserine, 1,2-distearoyl-sn-glycero-3-phosphate, 1,2-eistearoyl-sn-glycero-3-phosphocholine, 1,2-distearoyl-sn-glycero-3-phosphoethanolamine, 1,2-eistearoyl-sn-glycero-3-phosphoserine, hydrogenated egg phosphatidylcholine, hydrogenated soy phosphatidylcholine, egg-phosphatidylcholine, 1-myristoyl-sn-glycero-3-phosphocholine, 1-palmitoyl-sn-glycero-3-phosphocholine, 1-stearoyl-sn-glycero-3-phosphocholine, 1-myristoyl-2-palmitoyl-sn-glycero 3-phosphocholine, 1-myristoyl-2-stearoyl-sn-glycero-3-phosphocholine, 1-palmitoyl-2-myristoyl-sn-glycero-3-phosphocholine, 1-palmitoyl-2-oleoyl-sn-glycero-3-phosphocholine, 1-palmitoyl-2-oleoyl-sn-glycero-3-phosphoethanolamine, 1-palmitoyl-2-stearoyl-sn-glycero-3-phosphocholine, 1-stearoyl-2-myristoyl-sn-glycero-3-phosphocholine, 1-stearoyl-2-oleoyl-sn-glycero-3-phosphocholine, 1-stearoyl-2-palmitoyl-sn-glycero-3-phosphocholine, or a salt thereof (if applicable).

In some embodiments, the liposome composition may comprise a polymer. Suitable polymers include polyethyleneglycol (PEG) polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyaspartamide, and hydrophilic peptide sequences. In some embodiments, the polymer is a lipid-conjugated polymer. Examples of lipid-conjugated polymers include PEG-phospholipids, carbamate-linked PEG-phospholipids, monoacylglycerol-PEG, diacylglycerol-PEG, and polyacryloyl-phospholipids. In a specific embodiment, the polymer is 1,2-distearoyl-sn-glycero-3-phosphoethanolamine-N-[methoxy (polyethylene glycol)-2000]. In some embodiments, the liposome composition may comprise one or more additives. The one or more additives may be a stabilizing agent, a free-space-filling agent, an agent to limit lateral lipid diffusion, an agent to affect the phase transition of lipids, a diffusion coefficient altering agent, and an elastic modulus altering agent. In particular embodiments, cholesterol is used as a liposome composition additive.

In some embodiments, a liposome composition is a passive targeting liposome. In other embodiments, a liposome composition is an active targeting liposome. In some aspects, an active targeting liposome comprises at least one targeting moiety. Targeting moieties may be selected from the non-limiting group or targeting moieties that include antibodies, peptides, polymers, and small molecules.

In some embodiments, the liposome composition $^{19}$F-MR contrast molecule is at least one of

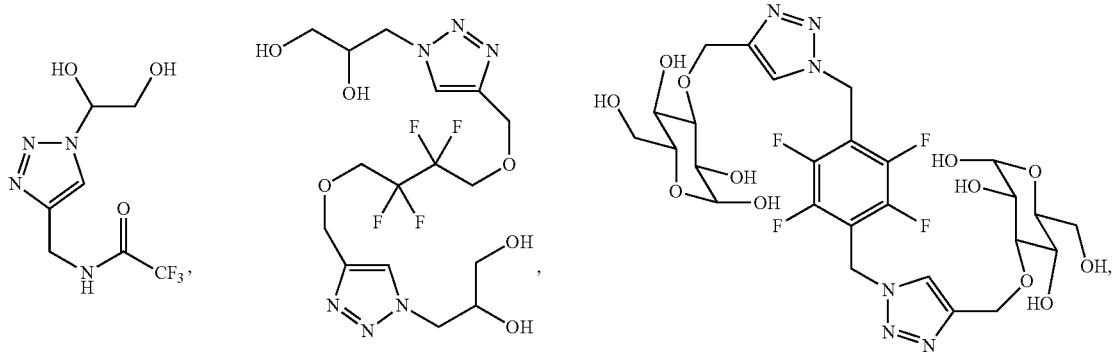

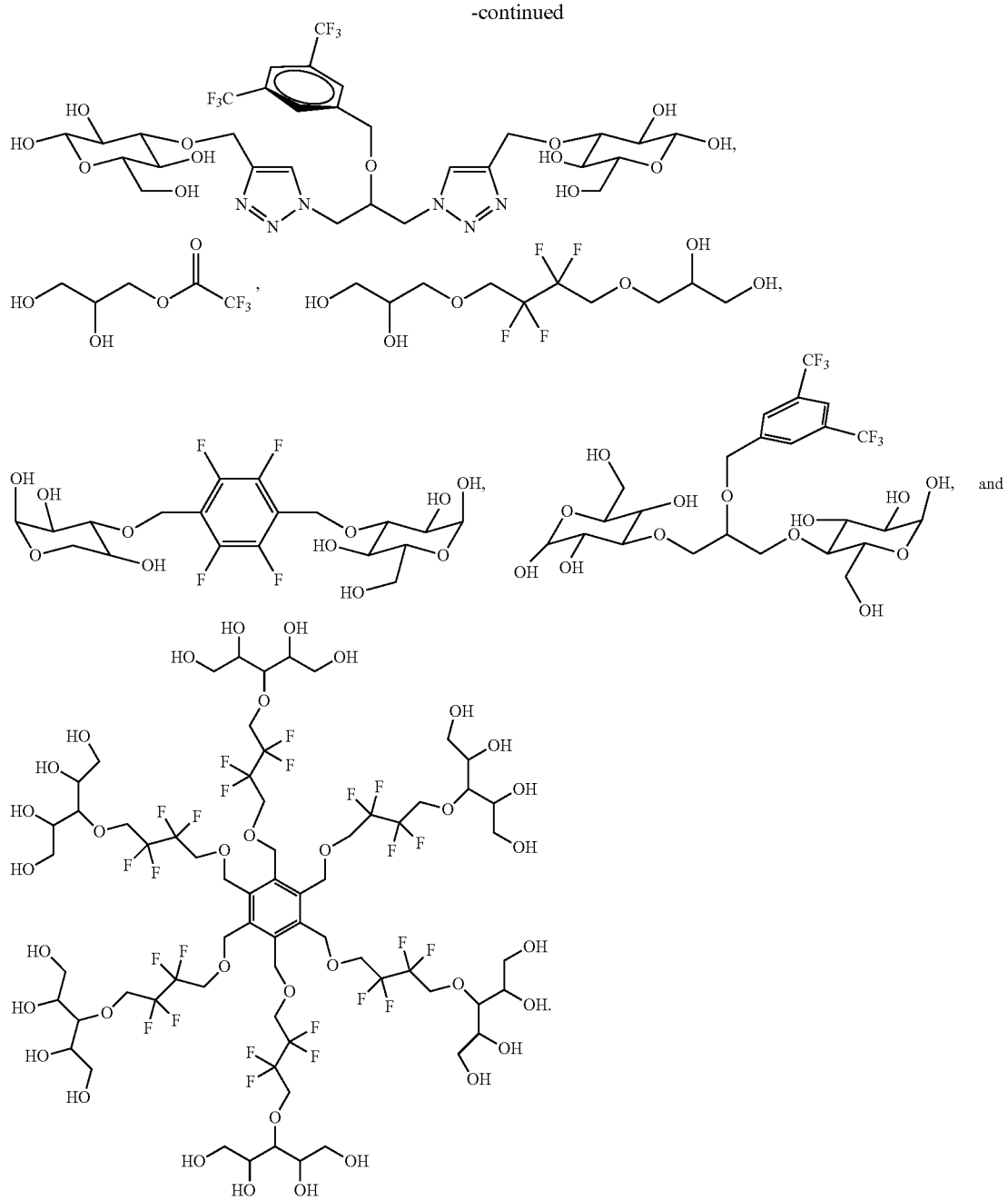

Some embodiments of the disclosure are directed towards a method of profiling multiple molecular species within a subject. In some aspects, the method comprises administering to the subject at least two $^{19}$F-MR contrast molecules with unique $^{19}$F-MR signals and imaging the contrast molecules with $^{19}$F MRI. In some embodiments, the at least two $^{19}$F-MR contrast molecules are at least two different $^{19}$F-MR contrast molecule formulations. A $^{19}$F-MR contrast molecule formulation may include a liposome, a tablet, buccal tablet, troche, capsule, elixir, suspension, syrup, wafer, and the like. The liposomes may be administered in a capsule, such as a gelatin capsule or a soft gel capsule as known in the art. In a specific embodiment, a $^{19}$F-MR contrast molecule liposome composition is a passive targeting liposome composition. In another embodiment, a $^{19}$F-MR contrast molecule liposome composition is an active targeting liposome composition In some embodiments, the at least two $^{19}$F-MR contrast molecules with unique $^{19}$F-MR signals are administered to different tissues. In some embodiments, the at least two $^{19}$F-MR contrast molecules with unique $^{19}$F-MR signals are targeted to different tissues. In some embodiments, targeting to different tissues comprises administering at least two $^{19}$F-MR contrast molecules by different routes. One non-limiting example of administration by different routes is administering one $^{19}$F-MR contrast molecule formulation orally and administering a different $^{19}$F-MR contrast molecule formulation intratumorally. In some embodiments, targeting to different tissues comprises administering at least two [19]F-MR contrast molecules with different tissue targeting propensities. In some embodiments, administering at least two [19]F-MR contrast molecules with different tissue targeting propensities comprises administering one [19]F-MR contrast molecule in an active targeting liposome and administering a different [19]F-MR contrast molecule in a passive targeting liposome. In some embodiments, administering at least two [19]F-MR contrast molecules with different tissue targeting propensities comprises administering one [19]F-MR contrast molecule in an active targeting liposome and administering a different [19]F-MR contrast molecule in an active targeting liposome with a different targeting moiety. In some embodiments, a method of profiling multiple molecular species within a subject comprises administering to the subject at least two [19]F-MR contrast molecules selected from the group consisting of

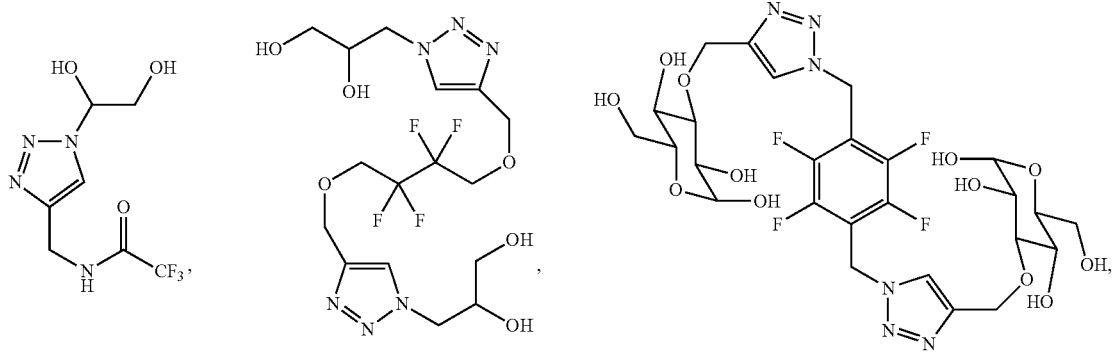

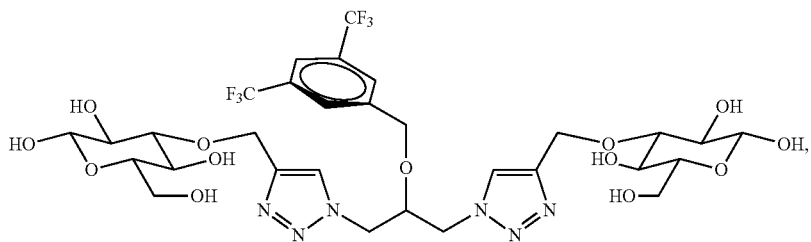

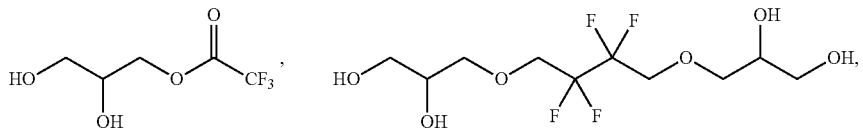

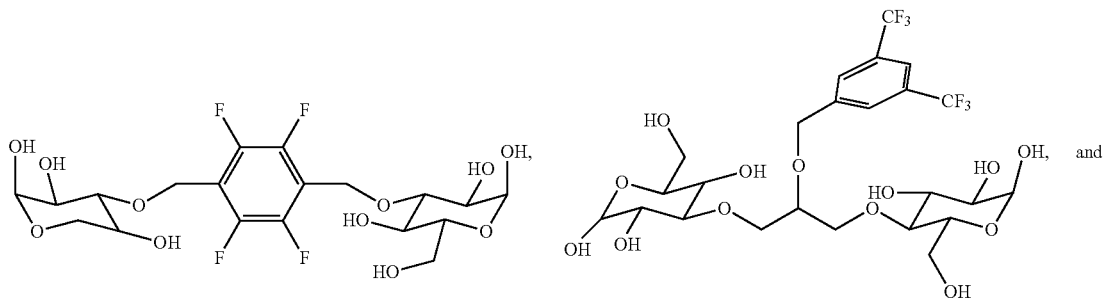

-continued

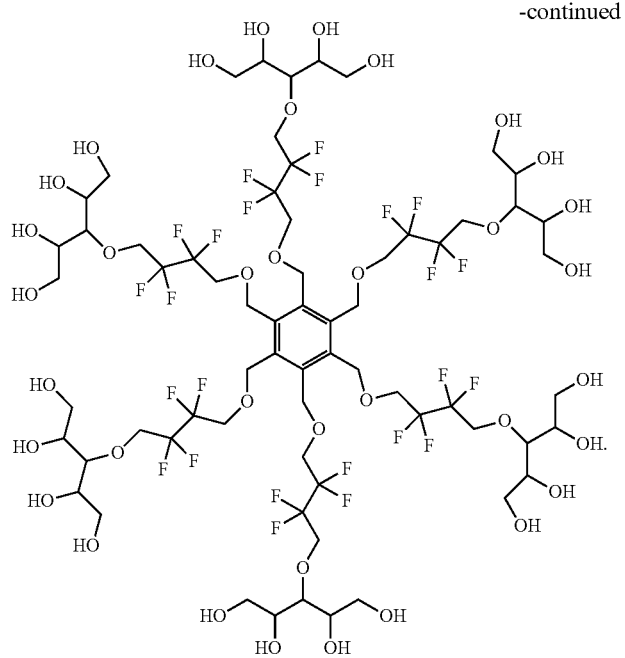

Any of the [19]F-MR contrast molecules described herein can be used in combination with one or more other [19]F-MR contrast molecules described herein in methods of profiling multiple molecular species or of imaging multiple biological features. The methods may include use of 2, 3, 4, 5, 6 or more of the [19]F-MR contrast molecules described herein. Compatible [19]F-MR contrast molecules for use in a single imaging experiment can be determined by the respective [19]F MR spectra of the molecules—if two different molecules have non-overlapping peaks on a [19]F MR spectrum, then they can be distinguished in a single imaging experiment. Thus, two or more different [19]F-MR contrast molecules can be used simultaneously to image different structural features in a single imaging experiment.

Some aspects of the disclosure are directed to a method of imaging a biological feature or structure, the method comprising contacting the biological feature or structure with a composition comprising any of the [19]F-MR contrast molecules disclosed herein and detecting the molecule with $^{19}$F-MRI. Contacting the biological feature with [19]F-MR contrast molecule may comprise administering the [19]F-MR contrast molecule to an organism, which may be a living organism. This may require preparing a formulation of the [19]F-MR contrast molecule with a pharmaceutically acceptable carrier or other biologically compatible composition so that the [19]F-MR contrast molecule can be brought into contact with the biological feature or structure.

The use of the word "a" or "an" when used in conjunction with the term "comprising" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

"Effective" or any variation of this term, when used in the claims or specification, means adequate to accomplish a desired, expected, or intended result.

The terms "about" or "approximately" are defined as being close to as understood by one of ordinary skill in the art, and in one non-limiting embodiment the terms are defined to be within 10%, preferably within 5%, more preferably within 1%, and most preferably within 0.5%.

The methods of introducing substances into cells disclosed herein can "comprise," "consist essentially of," or "consist of" particular components, compositions, ingredients, etc. disclosed throughout the specification.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description.

DETAILED DESCRIPTION OF THE INVENTION

Figure 1:
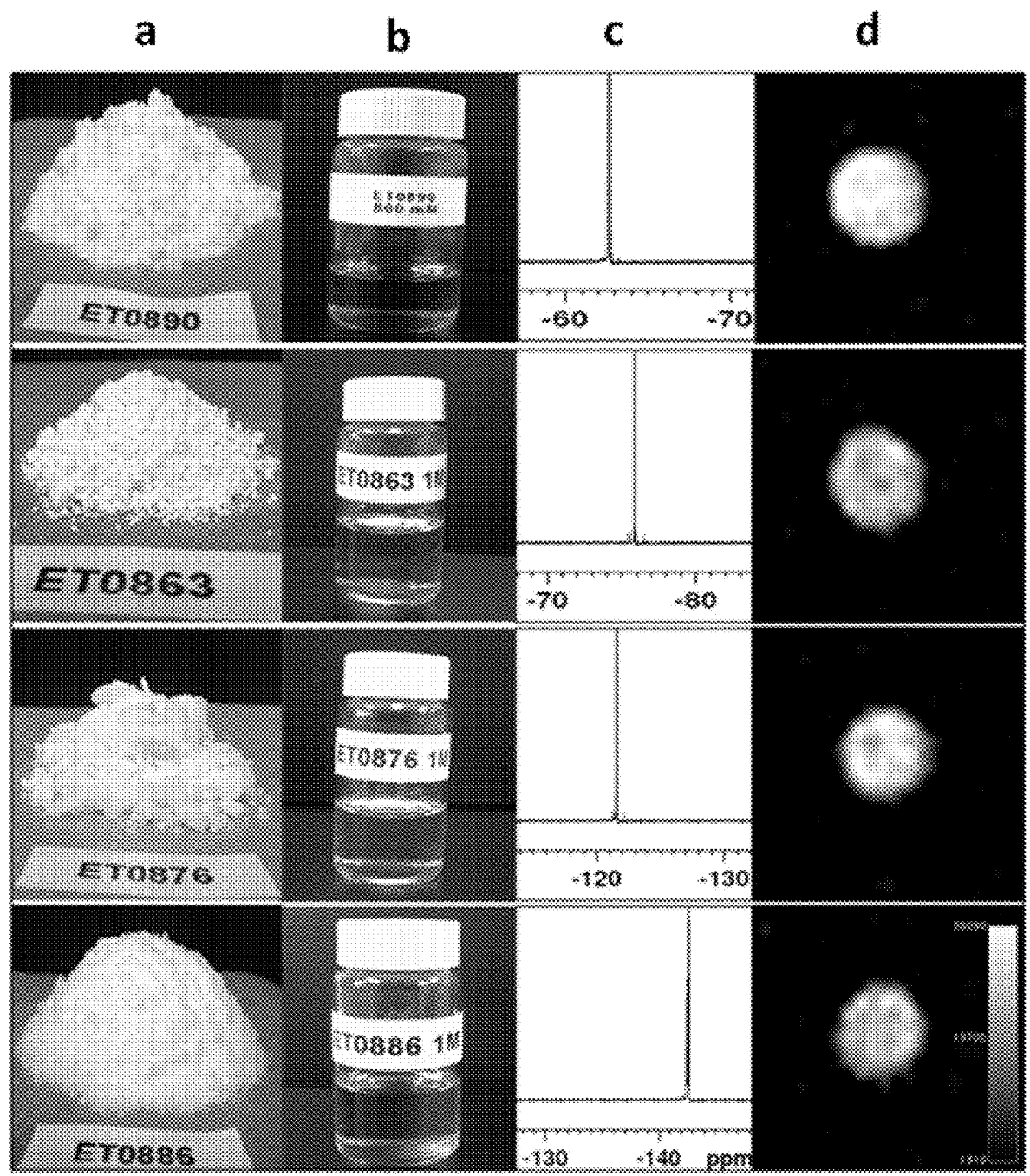
FIG. 1. Key physical and spectroscopic properties of hydrophilic fluorinated compounds (ET0890, ET0863, ET0876, and ET0886) for $^{19}$F MRI contrast media. (a) The four compounds are solids at room temperature. (b) The four compounds dissolve in aqueous media to give clear solutions at concentrations ≥1 M. (c)$^{19}$F NMR spectra of solutions of each compound give a single peak indicative of the magnetic and chemical purity. (d)[19]F MRI shows single sharp images of phantoms of each solution.

Novel $^{19}$F-MR contrast molecules are described herein, along with synthesis methods of such molecules, formulations that include such molecules, and methods of using such molecules. Non-limiting aspects of the present invention are discussed in further detail in the following sections.

I. Definitions

When used in the context of a chemical group, "hydrogen" means —H; "hydroxy" means —OH; "oxo" means =O; "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; "thio" means =S; "sulfonyl" means —S(O)$_2$—; and "sulfinyl" means —S(O)—.

In the context of chemical formulas, the symbol "—" means a single bond, "=" means a double bond; and "≡" means triple bond. The symbol "----" represents an optional bond, which if present is either single or double. The symbol "=====" represents a single bond or a double bond. Thus, for example, the structure

includes the structures

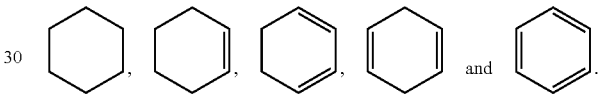

As will be understood by a person of skill in the art, no one such ring atom forms part of more than one double bond. The symbol "~~~", when drawn perpendicularly across a bond indicates a point of attachment of the group. It is noted that the point of attachment is typically only identified in this manner for larger groups in order to assist the reader in rapidly and unambiguously identifying a point of attachment. The symbol "◄■" means a single bond where the group attached to the thick end of the wedge is "out of the page." The symbol "⦀⦀⦀" means a single bond where the group attached to the thick end of the wedge is "into the page". The symbol "~~~" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

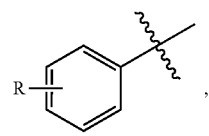

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

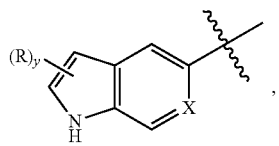

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C\le 8)}$" or the class "alkene$_{(C\le 8)}$" is two. For example, "alkoxy$_{(C\le 10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting examples of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl. The term "alkyl alcohol" is a subset of substituted alkyl, in which one or more hydrogen atoms has been substituted with a hydroxyl group (—OH).

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. When alkynyl is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

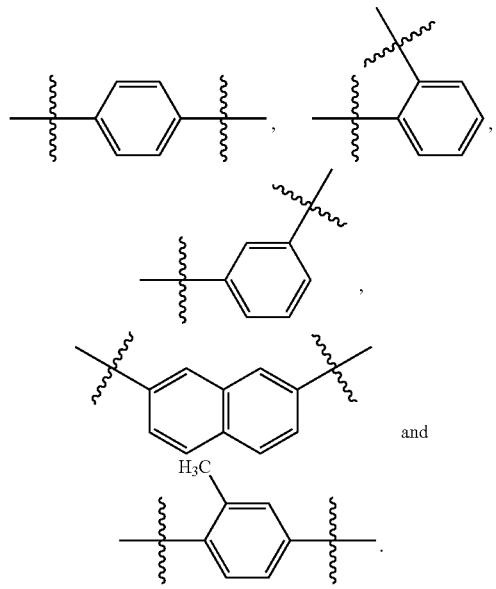

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

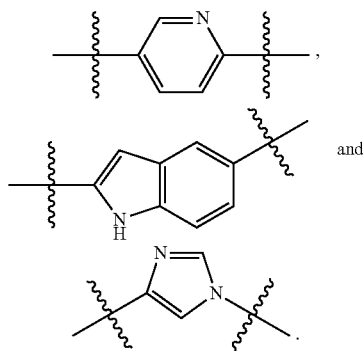

and

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. If more than one ring is present, the rings may be fused or unfused. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, and pyranyl. When the term "heterocycloalkyl" used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH (CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including the hydrogen atom directly attached the carbonyl or thiocarbonyl group) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkyl sulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O) NH$_2$, —OC(O)CH$_3$, or —S(O)$_2$NH$_2$. The groups —NHC (O)OCH$_3$ and —NHC(O)NHCH$_3$ are non-limiting examples of substituted amido groups.

As used herein, a "chiral auxiliary" refers to a removable chiral group that is capable of influencing the stereoselectivity of a reaction. Persons of skill in the art are familiar with such compounds, and many are commercially available.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2] oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

II. Formulations and Routes of Administration

In some aspects, the invention disclosed herein includes diagnostic compositions comprising one or more $^{19}$F MR contrast agents, which compositions may be administered to a subject, including to a mammal. For administration to a mammal, the diagnostic compositions may be combined with one or more excipients appropriate to the indicated route of administration. The diagnostic compositions may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and tableted or encapsulated for convenient administration. Alternatively, the diagnostic compositions may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art.

The diagnostic compositions may be subjected to conventional pharmaceutical operations such as sterilization and/or may contain conventional pharmaceutical carriers and excipients such as preservatives, stabilizers, wetting agents, emulsifiers, buffers, etc.

The diagnostic compositions described in the present disclosure may be administered by a variety of methods, e.g., orally or by injection (e.g. subcutaneous, intravenous, intraperitoneal, etc.). Depending on the route of administration, the diagnostic compositions may be coated in a material to protect the compositions from the action of acids and other natural conditions which may inactivate the compositions. They may also be administered by continuous perfusion/infusion of a disease or wound site.

To administer a diagnostic composition by other than parenteral administration, it may be necessary to coat the composition with, or co-administer the composition with, a material to prevent its inactivation. For example, a diagnosit compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The diagnostic compositions may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the diagnostic composition in the required amount in an appropriate solvent with one or a combination of ingredients enumerated above, as required, followed by filtered sterilization. Generally, dispersions are prepared by incorporating the diagnostic composition into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

A diagnostic composition can be orally administered, for example, with an inert diluent or an assimilable edible carrier. The diagnostic composition and other ingredients may also be enclosed in a hard or soft shell gelatin capsule, compressed into tablets, or incorporated directly into the subject's diet. For oral diagnostic administration, the diagnostic composition may be incorporated with excipients and used in the form of ingestible tablets, buccal tablets, troches, capsules, elixirs, suspensions, syrups, wafers, and the like. The percentage of the diagnostic composition in the compositions and preparations may, of course, be varied. The amount of the diagnostic composition in such diagnostically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of diagnostic composition calculated to produce the desired diagnostic effect in association with the required pharmaceutical carrier. The specification for the dosage unit forms of the invention are dictated by and directly dependent on (a) the unique characteristics of the diagnostic composition and the particular diagnostic effect to be achieved, and (b) the limitations inherent in the art of compounding such a diagnostic compound for imaging in a patient. Diagnostic compositions are administered at a diagnostically effective dosage sufficient to be imaged in a subject.

The actual dosage amount of a compound of the present disclosure or composition comprising a compound of the present disclosure administered to a subject may be determined by physical and physiological factors such as age, sex, body weight, severity of condition, the type of disease being diagnosed, previous or concurrent therapeutic interventions, idiopathy of the subject and on the route of administration. These factors may be determined by a skilled artisan. The practitioner responsible for administration will typically determine the concentration of diagnostic compound in a composition and appropriate dose(s) for the individual subject. The dosage may be adjusted by the individual physician in the event of any complication.

An effective amount for effective visualization of target tissues typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day.

In other non-limiting examples, a dose of a diagnostic compound or composition may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a diagnostic composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the $^{19}$F MR contrast agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

III. $^{19}$F MR Contrast Molecules

Figure 6A:
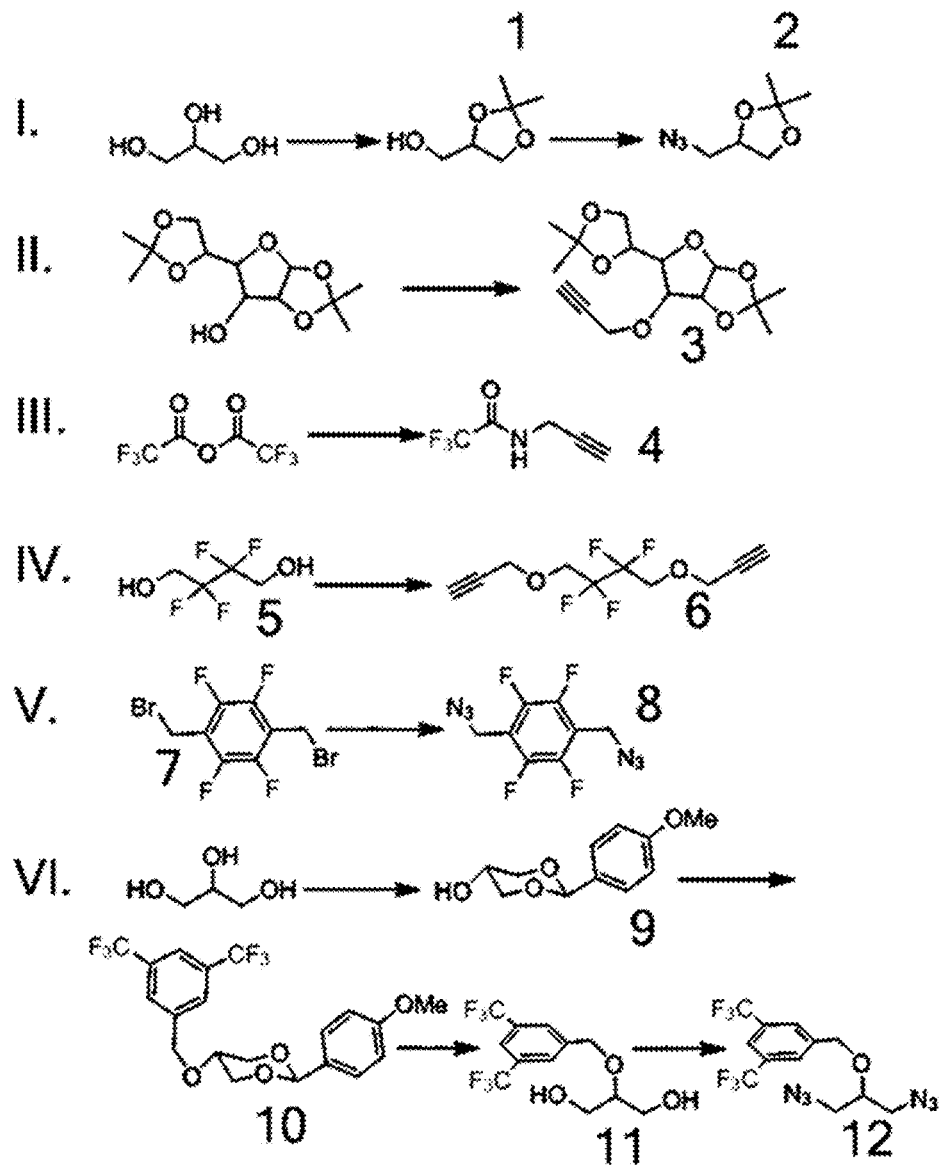
FIGS. 6A-6B depict synthetic schemes for compounds ET0890, ET0863, ET0876, and ET0886.
Figure 6B:
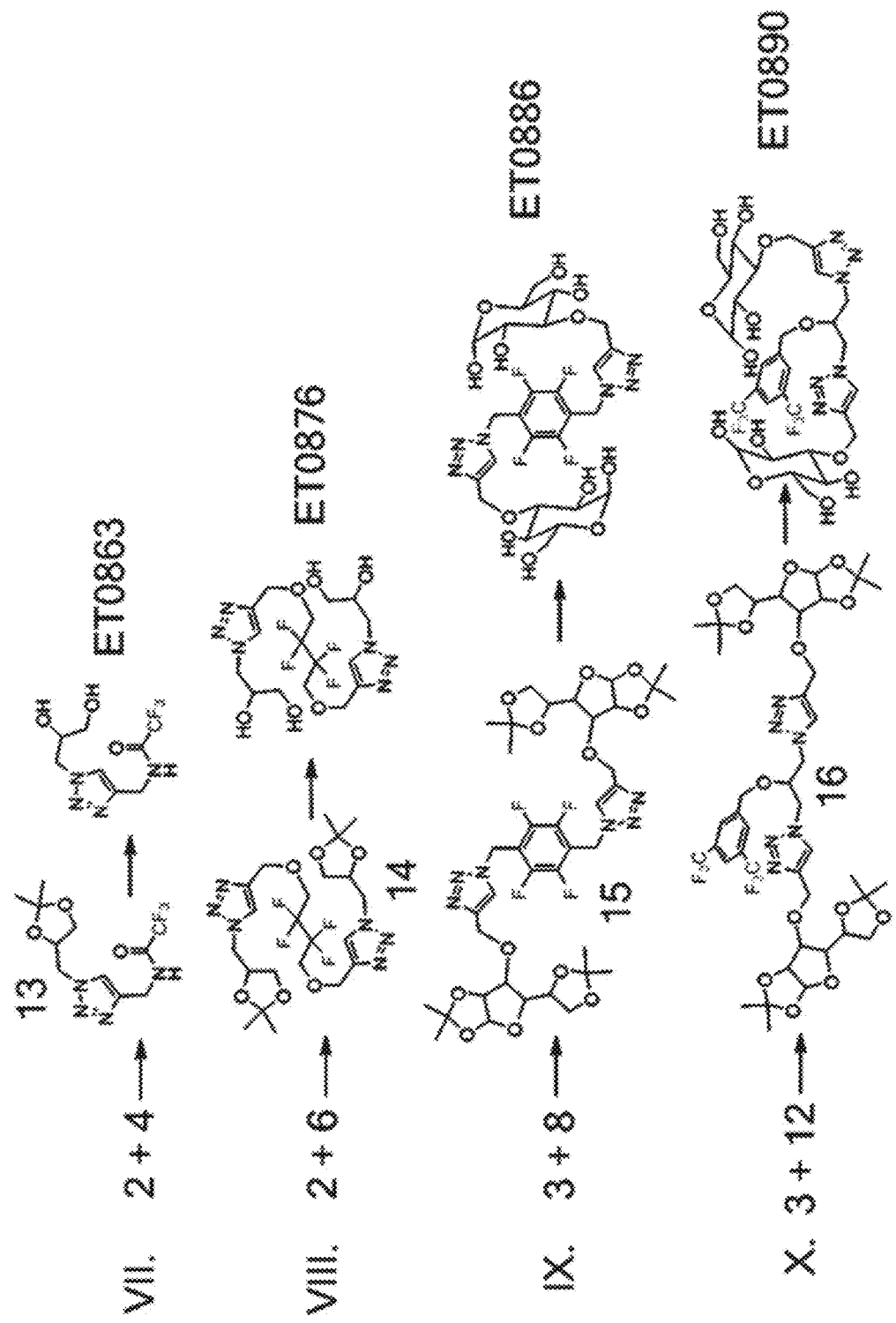

FIGS. 6A and 6B and Examples 2 to 19 below set forth synthesis pathways by which four $^{19}$F MR contrast molecules, ET0863, ET0876, ET0886, and ET0890, can be synthesized. The pathways include azide-based click chemistry and result in molecules with 1,2,3-triazole moieties. Different synthesis strategies may additionally be employed to synthesize the $^{19}$F MR contrast molecules disclosed herein. The synthesis strategies may result in different types of linkages between hydrophilic terminal moieties and $^{19}$F-containing core moieties. For example, FIGS. 7A and 7B and Example 22 below demonstrate synthesis of a $^{19}$F MR contrast molecule, ET1084, that includes terminal hydrophilic moieties linked to a $^{19}$F-containing core moiety via an ether linkage. Other linkages between hydrophilic terminal moieties and $^{19}$F-containing core moieties can also be used.

Figure 8:
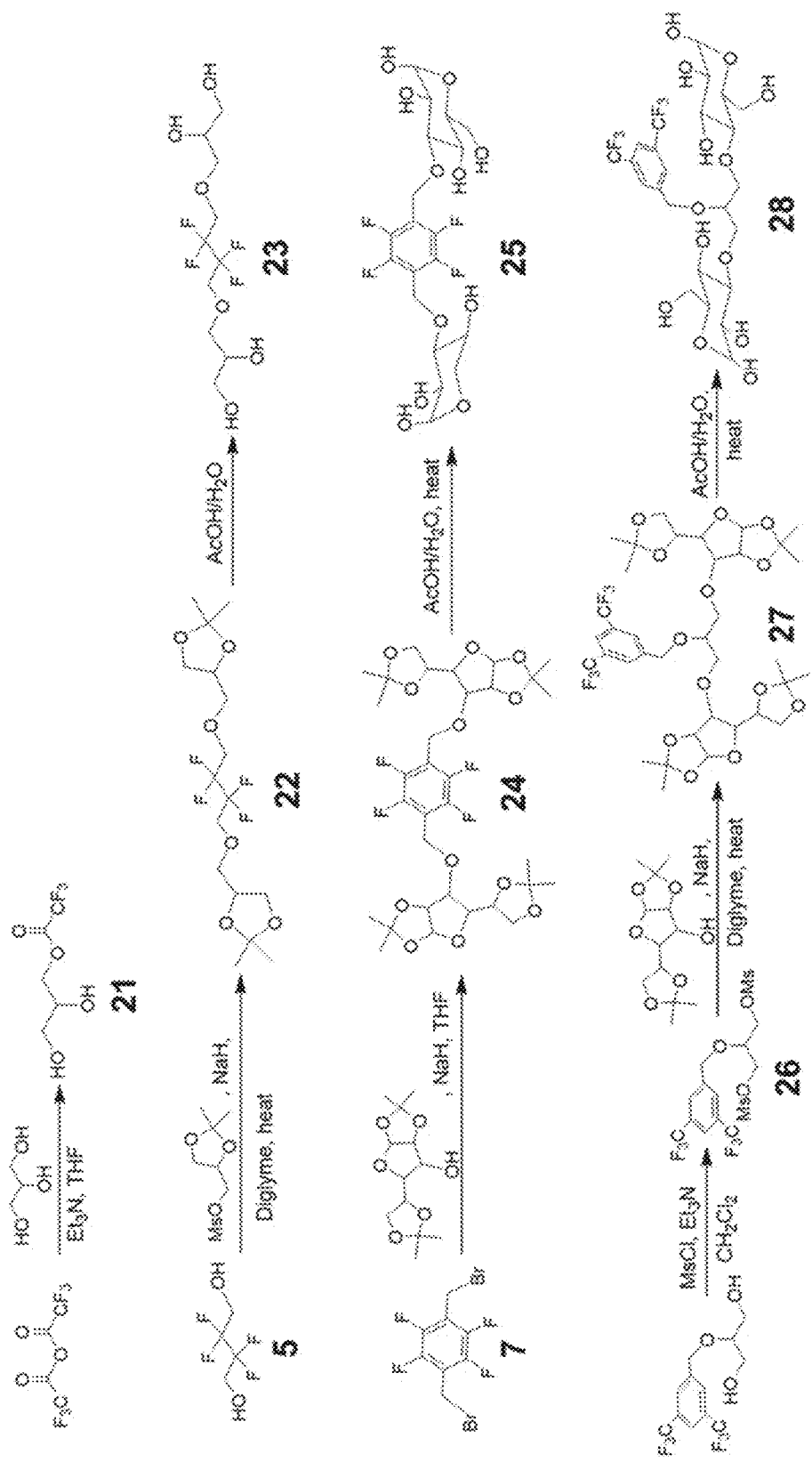
FIG. 8 depicts synthetic schemes for compounds 21, 23, 24, and 28.

FIG. 8 shows synthesis pathways by which additional $^{19}$F MR contrast molecules can be synthesized. Compounds 21, 23, 25, and 28 of FIG. 8 are analogous to molecules ET0863, ET0876, ET0886, and ET0890 of FIG. 6B, but have ether linkages between the nonionic hydrophilic moieties and the $^{19}$F-containing core moieties and do not have a 1,2,3-triazole moiety.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

There has been a tremendous increase in the understanding of heterogeneity in tumors [15] and cellular/molecular changes in several cancers over the past decade [2, 16]. Furthermore, molecular imaging-based dose painting studies using PET tracers have demonstrated the value of molecular painting in treatment, planning, and disease evaluation [17, 18]. There is therefore a growing need to develop non-invasive molecular imaging probes with the ability to simultaneously profile multiple molecular species/disease activity and disease subtypes within a target volume by molecular painting. $^{19}$F MRI probes have the potential to be molecular paints, but the field is currently dominated by PFCs and PFPEs which lack flexibility in formulation and do not allow individual imaging of diverse probes.

Several alternative $^{19}$F contrast formulation strategies addressing some of these limitations are under investigation and well documented in a recent review [10]. However, achieving a safely injectable formulation with any of these strategies remains a tall order. Partlow et al. have previously reported the ability to simultaneously track multiple targets in vivo using unique $^{19}$F MR signatures of PFC nanobeacons [19], the formulation of which have similar limitations as the PFC and PFPEs.

The molecules and methods disclosed herein are the first examples of a facile, versatile and highly reproducible approach to molecular painting by $^{19}$F MRI. Previous attempts at liposome formulations have focused on the use of perfluoro fatty acids or sulfonate amphiphiles to incorporate fluorine in the bilayer of the particle [20, 21], or the use of inorganic fluoride [22]. These approaches suffer from limited payload capacity and toxicity.

The hydrophilic organofluorine molecules disclosed herein allow facile synthetic access to water-soluble molecules with magnetically equivalent fluorine atoms which generate $^{19}$F MRI images with no chemical shift artifacts. When combined with the versatile liposome nanoparticle platform, they access the broad chemical shift spectrum of organofluorine species, enabling numerous targeted probes with unique $^{19}$F MR signatures. Such probes have the potential to enable noninvasive simultaneous visualization of multiple hot spots within the same region of interest (ROI), by $^{19}$F MRI as demonstrated in both phantom and in vivo assessment of the three formulations.

Isoflurane, the commonly used inhalable anesthesia in small animal studies, is fluorinated and highly lipophilic. It is therefore readily absorbed by adipose tissue in vivo. Its $^{19}$F MR signature is comparable to that of most PFCs and PFPEs. As shown in FIG. 7, this can greatly interfere with any signal from a PFC or PFPE probe, complicating data interpretation. Non-fluorinated injectable anesthesias such as ketamine and zylazine must therefore be used when running in vivo $^{19}$F MRI animal experiments with such probes. This is generally time consuming and in most cases greatly hinders work-flow. The approach disclosed herein allows for facile access to probes that can be imaged without interference from the isoflurane signal.

The most active formulation carries 22.7 mg $^{19}$F/mL, borne on a molecule with a molecular weight of 472.4 g/mol. Dimers and oligomers of these molecules can be readily accessed to increase the $^{19}$F content/particle of each formulation. In the dilution studies, a clear signal was observed after an 8-fold dilution. This corresponds to about 250 µL injected into the circulation of a 25 g mouse (blood volume~2 ml), about 2× lower than the maximum allowed volume, suggesting that the SNR should be sufficient for vascular imaging with each of these formulations.

Example 1

Materials and Methods

General Procedures.

2,2,3,3-Tetrafluoro-1,4-butanediol was purchased from Exfluor Research Corp., Round Rock, Tex., USA, and 1,4-bis(bromomethyl)-3,4,5,6-tetrafluorobenzene (7) was purchased from Molport, Riga, Latvia. All other reagents, including redistilled analytical grade trifluoroacetic acid, were obtained from Sigma-Aldrich and used without further purification. Proton nuclear magnetic resonances ($^{1}$H NMR) spectra were recorded at 600 MHz on a Bruker 600 NMR spectrometer or at 300 MHz on a Bruker 300 NMR spectrometer. Carbon nuclear magnetic resonances ($^{13}$C NMR) spectra were recorded at 150 MHz on a Bruker 600 NMR spectrometer or at 75 MHz on a Bruker 300 NMR spectrometer. Fluorine nuclear magnetic resonances ($^{19}$F NMR) spectra were recorded at 282 MHz on a Bruker 300 NMR spectrometer. Chemical shifts are reported in parts per million (ppm) from an internal standard acetone (2.05 ppm), chloroform (7.26 ppm), or water (4.79 ppm) for $^{1}$H NMR; and from an internal standard of either residual acetone (206.26 ppm), chloroform (77.00 ppm), or dimethyl sulfoxide (39.52 ppm) for $^{13}$C NMR. NMR peak multiplicities are denoted as follows: s (singlet), d (doublet), t (triplet), q (quartet), p (pentet), bs (broad singlet), dd (doublet of doublet), tt (triplet of triplet), ddd (doublet of doublet of doublet), and m (multiplet). Coupling constants (J) are given in hertz (Hz). High resolution mass (HRMS) spectra were obtained from the Mass Spectrometry Unit of the Bioscience Research Collaborative at Rice University, Houston, Tex. Thin layer chromatography (TLC) was performed on silica gel 60 F254 plates from EMD Chemical Inc. and components were visualized by ultraviolet light (254 nm) and/or phosphomolybdic acid, 20 wt % solution in ethanol. SiliFlash silica gel (230-400 mesh) was used for all column chromatography.

Example 2

Chemical Synthesis Procedure for Compound 1 in FIG. 6A

FIGS. 6A-6B set forth the synthetic schemes for $^{19}$F MR contrast agents disclosed herein. In this Example and in further Examples that follow, additional details are provided for the chemical synthesis procedures for compounds shown in FIGS. 6A-6B.

Compound 1 in FIG. 6A: To a solution of compound glycerol (50.00 g, 542.9 mmol), in acetone (2 L), was added 2,2-dimethoxypropane (100 mL, 806.0 mmol), followed by p-toluenesulfonic acid (1.03 g, 5.429 mmol). The mixture was stirred at ambient temperature for 12 hours, followed by addition of solid anhydrous potassium carbonate (6.00 g, 4.34 mmol). The mixture was stirred for a further 30 mins followed by filtration of solids. The filtrate was concentrated by rotary evaporation to obtain the desired acetonide 1, quantitatively as a clear residue, used in subsequent steps without further purification. $^{1}$H NMR (300 MHz, CDCl$_3$) δ 4.4.14 (p, J=4.8 Hz, 1H), 3.96 (dd, J=8.4, 6.6 Hz, 1H), 3.69 (dd, J=9.6, 6.0 Hz, 1H), 3.60 (dd, J=12.0, 4.8 Hz, 1H), 3.52 (dd, J=12.0, 4.8 Hz, 1H), 3.13 (s, 1H/OH), 1.35 (s, 3H), 1.29 (s, 3H); $^{13}$C NMR (CDCl$_3$, 150 MHz) δ 109.30, 76.21, 65.81, 62.94, 26.59, 25.18. The synthetic schemes are outlined in FIGS. 6A-6B.

Example 3

Procedure for Compound 2 in FIG. 6A

To a solution of compound 1 (50.00 g, 378.3 mmol), in pyridine (500 mL), cooled in an ice/water bath, was added p-toluenesulfonyl chloride (93.70 g, 491.8 mmol). The mixture was stirred at 4° C. for 12 hours, followed by removal of pyridine by rotary evaporation. The residue was diluted with 500 mL 1N HCl and extracted (3×) with diethyl ether. The combined organic extracts were rinsed with brine, dried over MgSO$_4$ and concentrated by rotary evaporation to obtain a clear residue which was dissolved in DMF (400 mL) followed by addition of NaN$_3$ (92.00 g, 1.4 mol). The ensuing mixture was heated at 70° C. for 12 hours, after which it was cooled down to ambient temperature and filtered through a pad of celite. The filtrate was diluted with water and extracted (3×) with diethyl ether. The combined organic extracts were rinsed with brine, concentrated by evaporation to obtain a clear residue. This was subjected to column chromatography on silica gel eluted with a diethyl ether/pentane mixture (1:9), to obtain 2 as clear oil (32.80 g, 65% yield over two steps). $^{1}$H NMR (300 MHz, CDCl$_3$) δ 4.21 (p, J=6 Hz, 1H), 3.99 (dd, J=8.4, 6.0 Hz, 1H), 3.70 (dd, J=8.4, 6.0 Hz, 1H), 3.33 (dd, J=13.2, 4.8 Hz, 1H), 3.23 (dd, J=13.2, 4.8 Hz, 1H), 1.40 (s, 3H), 1.30 (s, 3H); $^{13}$C NMR (75 MHz, CDCl$_3$) δ 109.81, 74.53, 66.47, 52.73, 26.50, 25.12.

Example 4

Procedure for Compound 3 in FIG. 6A

To a suspension of NaH (60% in mineral oil, 3.458 g, 144.1 mmol), in THF (500 mL), cooled in an ice/water bath was added diacetone glucose (25.00 g, 96.05 mmol). The mixture was stirred at 0° C. for 30 mins, followed by addition of propargyl bromide (17.1 mL, 115.3 mmol), and the ensuing mixture allowed to warm to ambient temperature overnight. Unreacted NaH was quenched by pouring the reaction mixture into crushed ice and further diluted with water, resulting in two phases. The organic phase was removed and the aqueous phase extracted (2×) with diethyl ether. The combined organic extracts were rinsed with brine, dried over MgSO$_4$ and concentrated. The ensuing brown residue was subjected to column chromatography on silica gel eluted with 10% ethyl acetate/hexanes mixture to obtain compound 3 as pale yellow oil (16.50 g, 55% yield). $^{1}$H NMR (600 MHz, CDCl$_3$) δ 5.87 (d, J=3.6 Hz, 1H), 4.62 (d, J=4.2 Hz, 1H), 4.28 (m, 3H), 4.13 (dd, J=7.2, 3.0 Hz, 1H), 4.08 (m, 2H), 3.98 (dd, J=8.4, 5.4 Hz, 1H), 2.49 (t, J=2.4 Hz, 1H), 1.49 (s, 3H), 1.41 (s, 3H), 1.34 (s, 3H), 1.31 (s, 3H); $^{13}$C NMR (150 MHz, CDCl$_3$) δ 111.85, 108.99, 105.20, 82.82, 81.52, 80.99, 79.26, 74.96, 72.51, 67.17, 58.08, 26.81 (2C), 26.23, 25.36.

Example 5

Procedure for Compound 4 of FIG. 6A

To a stirred mixture of propargylamine (4.0 mL, 62.45 mmol) and diisopropylethylamine (21.8 mL, 124.9 mmol), in THF (150 mL) at 0° C. was added trifluoroacetic anhydride (13.1 mL, 93.68 mmol) drop wise. The mixture was allowed to warm to room temperature over 3 hours, at which point the reaction was judged complete by TLC. The mixture was poured into 1N HCl solution (300 mL) an extracted (3×) with ethyl acetate. The combined organic extracts were rinsed sequentially with saturated $NaHCO_3$ solution and brine, dried over $Na_2SO_4$ and concentrated to obtain the crude product. This was further purified by column chromatography on silica gel eluted with 15-30% ethyl acetate/hexanes gradient to afford 4 as pale yellow oil (8.680 g, 92% yield). $^1H$ NMR (300 MHz, $CDCl_3$) δ 7.34 (bs, NH), 4.14 (s, 2H), 2.32 (s, 1H); $^{19}F$ NMR (282 MHz, $CDCl_3$) δ −76.11; $^{13}C$ NMR (75 MHz, $CDCl_3$) δ 157.34 (q, J=9.4 Hz), 115.59 (q, J=71.3 Hz), 72.84, 29.59.

Example 6

Procedure for Compound 6 of FIG. 6A

Compound 5 (10.00 g, 61.70 mmol) was added to a suspension of NaH (60% in mineral oil, 3.702 g, 154.2 mmol), in THF (300 mL), cooled in an ice/water bath. The mixture was stirred at 0° C. for 30 mins, followed by addition of propargyl bromide (22.1 mL, 148.1 mmol), and the ensuing mixture allowed to warm to ambient temperature overnight. The reaction was quenched by pouring into crushed ice, extracted with ether, rinsed with brine, and dried over anhydrous $Na_2SO_4$. Following filtration, the solvent was removed in vacuo to give a crude mixture which was purified by column chromatography on silica gel eluted with 10% ethyl acetate/hexanes to obtain 6 (13.80 g, 94% yield) as a colorless oil. $^1H$ NMR (300 MHz, $CDCl_3$) δ 4.29 (d, J=2.4, 4H), 3.99 (tt, J=14.2, 2.6 Hz, 4H), 2.54 (t, J=2.4, 2H); $^{19}F$ NMR (282 MHz, $CDCl_3$) δ −121.69; $^{13}C$ NMR (75 MHz, $CDCl_3$) δ 115.96 (tt, J=62.8, 7.7 Hz), 78.00, 75.97, 65.94 (t, J=6.4 Hz), 59.24.

Example 7

Procedure for Compound 8 of FIG. 6A $NaN_3$ (19.35 g, 297.9 mmol) was added to a solution of 7 (10.00 g, 29.77 mmol) in anhydrous DMF (150.0 mL) and the resulting mixture heated at 70° C. for 5 h, after which it was cooled to room temperature. The solids were filtered off and the filtrate concentrated in vacuo. The ensuing residue was diluted with water and extracted (3×) with diethyl ether. The combined organic extracts were dried over $Na_2SO_4$ and concentrated to obtain 8 as a pale orange solid (7.580 g, 98% yield), which gave a single spot on TLC, and was used in the next step without further purification. $^1H$ NMR (300 MHz, $CDCl_3$) δ 4.51 (s, 4H); $^{19}F$ NMR (282 MHz, $CDCl_3$) δ −142.24; $^{13}C$ NMR (75 MHz, $CDCl_3$) δ 144.94 (dm, J=50.5 Hz, 4C), 115.13 (m, 2C), 41.90 (t, J=2.3 Hz).

Example 8

Procedure for Compound 9 of FIG. 6A

To a stirred mixture of glycerol (31.54 g, 342.5 mmol), p-anisaldehyde (50.0 mL, 410.9 mmol), 4 Å molecular sieves (20.0 g) in anhydrous DMF (200 mL) was added p-toluene sulfonic acid (3.250 g, 17.09 mmol). The mixture was stirred for 12 h, after which it was poured into saturated $NaHCO_3$ solution and extracted with diethyl ether. The combined organic extracts were rinsed with brine, and dried over anhydrous $Na_2SO_4$. Following filtration, the solvent was removed in vacuo to give a crude mixture which was purified by chromatography on silica gel eluted with 30-50% ethyl acetate/hexanes gradient. Fractions containing 9 gave a white solid upon concentration (36.5 g, 51% yield). $^1H$ NMR (300 MHz, $CDCl_3$) δ 7.43 (d, J=8.7 Hz, 2H), 6.93 (d, J=8.7 Hz, 2H), 5.34 (s, H), 4.20 (dd, J=10.5, 4.8 Hz, 2H), 3.85 (m, 1H), 3.78 (s, 3H), 3.48 (t, J=11.1, 2H), 3.36 (m, 1H); $^{13}C$ NMR (75 MHz, $CDCl_3$) δ 160.17, 129.92, 127.57, 113.78, 100.99, 71.64, 60.98, 55.34.

Example 9

Procedure for Compound 10 of FIG. 6A

Alcohol 9 (8.4 g, 61.7 mmol) was added to a suspension of NaH (60% in mineral oil, 1.4 g, 58.0 mmol), in THF (250 mL), cooled in an ice/water bath. The mixture was stirred at 0° C. for 30 mins, followed by addition of 3,5-bis(trifluoromethyl)benzyl bromide (10 g, 32.6 mmol), and the ensuing mixture allowed to warm to ambient temperature for 12 h. The reaction was quenched by pouring into crushed ice, extracted with ether, rinsed with brine, and dried over anhydrous $Na_2SO_4$. Following filtration, the solvent was removed in vacuo to give a crude mixture. This was purified by chromatography on silica gel with 5-10% ethyl acetate/hexanes gradient as eluent, to obtain 10 (13.4 g, 96% yield) as a white solid. $^1H$ NMR (300 MHz, $CDCl_3$) δ 7.88 (s, 1H), 7.82 (s, 2H), 7.46 (d, J=8.6, 2H), 6.95 (d, J=8.6, 2H), 5.44 (s, 1H), 4.70 (s, 2H), 4.45 (dd, J=8.4, 4.5 Hz, 2H), 3.88 (m, 1H), 3.83 (s, 3H), 3.70 (m, 2H); $^{19}F$ NMR (282 MHz, $CDCl_3$) δ −62.90; $^{13}C$ NMR (75 MHz, $CDCl_3$) δ 160.18, 140.74, 131.80 (q, J=33.8 Hz, 2C), 130.02, 127.43, 127.17 (d, J=3 Hz), 123.32 (q, J=270.8 Hz), 121.71 (p, J=3.8 Hz), 69.98, 69.82, 68.86, 55.21.

Example 10

Procedure for Compound 11 of FIG. 6A

Compound 10 (12.5 g, 28.6 mmol) was dissolved in 80% $AcOH/H_2O$ mixture (200 mL), by warming in a water bath at 50° C. The solution was then allowed to stir at room temperature for 12 h. The solvents were removed by rotary evaporation and the resulting residue chromatographed on silica gel eluted with 40-60% ethyl acetate/hexanes gradient to diol 11, as clear oil (8.3 g, 91% yield). $^1H$ NMR (300 MHz, $CDCl_3$) δ 7.83 (s, 2H), 7.81 (s, 1H), 4.76 (s, 2H), 3.85 (dd, J=11.7, 4.8 Hz, 2H), 3.76 (dd, J=11.7, 4.8 Hz, 2H), 3.60 (p, J=4.5, 1H), 3.50 (bs, 2H); $^{19}F$ NMR (282 MHz, $CDCl_3$) δ −62.98; $^{13}C$ NMR (75 MHz, $CDCl_3$) δ 140.81, 132.10, 131.67 (q, J=8.3 Hz, 2C), 127.38 (d, J=3.0 Hz), 123.26 (q, J=271.5 Hz), 121.56 (p, J=3.0 Hz), 114.34, 80.02, 70.31, 61.96.

Example 11

Procedure for Compound 12 of FIG. 6A

To a solution of compound 11 (8.0 g, 25.6 mmol), in pyridine (150 mL), cooled in an ice/water bath was added p-toluenesulfonyl chloride (14.7 g, 76.9 mmol). The mixture was stirred at 4° C. for 12 hours, followed by removal of pyridine by rotary evaporation. The residue was diluted with 200 mL dichloromethane, rinsed with 1N HCl solution, dried over $MgSO_4$ and concentrated by rotary evaporation to obtain a clear residue (16.1 g). This was dissolved in DMF (150 mL) followed by addition of $NaN_3$ (16.6 g, 256.2 mol). The ensuing mixture was heated at 70° C. for 5 hours, after which it was cooled down to ambient temperature and filtered through a pad of celite. The filtrate was diluted with water and extracted (3×) with diethyl ether. The combined organic extracts were rinsed with brine, concentrated by rotary evaporation to obtain a clear residue. This was subjected to column chromatography on silica gel eluted with 10% ethyl acetate/hexanes mixture (1:9), to obtain 12 as clear oil (7.9 g, 84% yield over two steps). $^1$H NMR ($CDCl_3$, 300 MHz) δ 7.88 (s, 2H), 7.86 (s, 1H), 4.84 (s, 2H), 3.78 (p, J=5.1, Hz, 1H), 3.49 (d, J=5.1, 4H)); $^{19}$F NMR (282 MHz, $CDCl_3$) δ −63.03; $^{13}$C NMR (75 MHz, $CDCl_3$) δ 140.08, 131.78 (q, J=33.0 Hz, 2C), 127.35, 123.29 (q, J=271 Hz), 78.92, 70.94, 51.98.

Example 12

Procedure for Compound 13 of FIG. 6B

To a solution of 4 (8.0 g, 52.9 mmol), 2 (10.0 g, 63.5 mmol), and sodium ascorbate (1.0 g, 5.3 mmol) in a mixture of methanol/ethyl acetate/water (5:2:2, 180 mL) was added $Cu(OAc)_2$ (528.6 mg, 2.6 mmol). The mixture was stirred at room temperature for 12 h then poured into a brine/water mixture (1:1, 200 mL), extracted with ethyl acetate (200 mL, 3 times). The combined organic phases were dried over $Na_2SO_4$, filtered, and upon concentration gave a white solid which was washed with a mixture of ethyl acetate/hexanes to obtain 13, as a white crystalline solid (13.7 g, 84% yield). $^1$H NMR (300 MHz, $CDCl_3$) δ 8.45 (s, NH), 7.80 (s, 1H), 4.61-4.39 (m, 5H), 4.13 (m, 1H), 3.75 (m, 1H); $^{19}$F NMR (282 MHz, $CDCl_3$) δ −75.82; $^{13}$C NMR (75 MHz, $CDCl_3$) δ 157.52 (q, J=35.25 Hz), 142.79, 124.43, 115.81 (q, J=268.5 Hz), 110.34, 73.84, 66.26, 52.49, 34.81, 26.56, 25.08.

Example 13

Procedure for Compound 14 of FIG. 6B

To a solution of 6 (6.0 g, 25.2 mmol), 2 (9.9 g, 63.0 mmol), and sodium ascorbate (1.0 g, 5.0 mmol) in a mixture of methanol/ethyl acetate/water (5:2:2, 180 mL), was added $Cu(OAc)_2$ (503 mg, 2.5 mmol). The mixture was stirred at room temperature for 12 h, then poured into a brine/water mixture (1:1, 200 mL), and extracted with ethyl acetate (200 mL, 3 times). The combined organic phases were dried over $Na_2SO_4$, filtered, and concentrated. The ensuing residue was chromatographed on silica gel eluted with 30-50% ethyl acetate/hexanes gradient, then a mixture of ethyl acetate/hexanes/methanol (5:4:1) to afford 14 as a white solid (11.7 g, 98% yield). $^1$H NMR (300 MHz, $CDCl_3$) δ 7.76 (s, 2H), 4.75 (s, 4H), 4.58-4.40 (m, 6H), 4.10 (dd, J=10.5, 8.7 Hz, 2H), 3.95 (t, J=14.1 Hz, 4H), 3.75 (dd, J=8.7, 5.7 Hz, 2H); $^{19}$F NMR (282 MHz, $CDCl_3$) δ −121.72; $^{13}$C NMR (75 MHz, $CDCl_3$) δ 143.83, 124.34, 110.22, 73.97, 66.91 (t, J=25.5 Hz), 66.40, 65.52, 52.36, 30.89, 26.64, 25.15.

Example 14

Procedure for Compound 15 of FIG. 6B

To a solution of 8 (6.8 g, 26.1 mmol), 3 (23.4 g, 78.4 mmol), and sodium ascorbate (1.0 g, 5.2 mmol) in a mixture of methanol/ethyl acetate/water (3:1:1, 200 mL) was added $Cu(OAc)_2$ (521.9 mg, 2.6 mmol). The mixture was stirred at room temperature for 12 h after which the solvent was stripped in vacuo. The residue was diluted with water (200 mL), extracted with ethyl acetate (200 mL, 3 times). The combined organic phases were rinsed with brine, dried over $Na_2SO_4$, filtered, and concentrated. The ensuing residue was chromatographed on silica gel eluted with 30-50% ethyl acetate/hexanes gradient, then a mixture of ethyl acetate/hexanes/methanol (60:35:5) to afford 15 as a clear viscous paste which upon cooling and vacuum drying, foams into a white glassy solid (23.3 g, 94% yield). $^1$H NMR (300 MHz, $CDCl_3$) δ 7.73 (s, 2H), 5.86 (d, J=3.6 Hz, 2H), 5.65 (s, 4H), 4.79 (dd, J=15.0, 12.6 Hz, 4H), 4.60 (d, J=3.6 Hz, 2H), 4.29 (m, 2H), 4.07 (m, 8H), 1.48 (s, 6H), 1.41 (s, 6H), 1.35 (s, 6H), 1.30 (s, 6H). $^{19}$F NMR (282 MHz, $CDCl_3$) δ −140.86; $^{13}$C NMR (75 MHz, $CDCl_3$) δ 145.59, 122.74, 114.74, 111.89, 105.20, 82.56, 81.87, 81.06, 72.30, 67.43, 63.98, 41.08, 26.85, 26.77, 26.18, 25.39.

Example 15

Procedure for Compound 16 of FIG. 6B

To a solution of 12 (6.0 g, 16.3 mmol), 3 (12.2 g, 40.8 mmol), and sodium ascorbate (711.3 mg, 3.6 mmol) in a mixture of methanol/ethyl acetate/water (3:1:1, 200 mL) was added $Cu(OAc)_2$ (325.8 mg, 1.6 mmol). The mixture was stirred at room temperature for 12 h after which the solvent was stripped in vacuo. The residue was diluted with water (200 mL), extracted with ethyl acetate (200 mL, 3 times). The combined organic phases were rinsed with brine, dried over $Na_2SO_4$, filtered, and concentrated. The ensuing residue was chromatographed on silica gel eluted with 30-50% ethyl acetate/hexanes gradient, then a mixture of ethyl acetate/hexanes/methanol (60:35:5) to afford 16 as a clear viscous paste which upon cooling and vacuum drying, foams into a white glassy solid (15.3 g, 97% yield). $^1$H NMR (300 MHz, $CDCl_3$) δ 7.82 (s, 1H), 7.73 (s, 2H), 7.59 (s, 2H), 5.86 (d, J=3.9 Hz, 2H), 4.80 (s, 4H), 4.59 (s, 4H), 4.52 (m, 4H), 4.29 (m, 2H), 4.07 (m, 8H), 1.48 (s, 6H), 1.39 (s, 6H), 1.30 (s, 6H), 1.29 (s, 6H). $^{19}$F NMR (282 MHz, $CDCl_3$) δ −62.98; $^{13}$C NMR (75 MHz, $CDCl_3$) δ 145.23, 139.24, 131.95 (q, J=33.0 Hz), 127.23, 124.87, 124.28, 124.25, 122.12, 121.25, 111.88, 109.05, 105.20, 82.73, 82.70, 81.99, 81.04, 72.37, 71.29, 67.36, 63.95, 26.82, 26.76, 26.16, 25.41.

Example 16

Final Step to ET0863 of FIG. 6B

To a solution of 13 (5.0 g, 16.2 mmol) in methanol (160 mL) was added TsOH (617.0 mg, 3.2 mmol). The mixture was stirred at room temperature for 12 h after which the solvent was stripped in vacuo. The residue was diluted with mixture of brine and saturated $NaHCO_3$ (1:1, 200 mL), extracted with ethyl acetate (200 mL, 3 times). The combined organic phases were dried over $Na_2SO_4$, filtered, and concentrated down to 100 mL. Upon adding a few drops of hexanes, the product precipitated out of solution and was filtered to obtain ET0863 as a white solid (3.8 g, 87% yield). $^1$H NMR (300 MHz, $D_2O$) δ 7.99 (s, H), 4.1 (s, 2H), 4.58 (dd, J=8.7, 2.1 Hz, 1H), 4.44 (dd, J=8.7, 4.8 Hz, 1H), 4.13 (m, 1H), 3.65 (dd, J=7.2, 3.0 Hz, 1H), 3.57 (dd, J=7.2, 3.6 Hz, 1H); $^{19}$F NMR (282 MHz, $D_2O$) δ −75.90; $^{13}$C NMR (75 MHz, $D_2O$) δ 158.85 (q, J=22.5 Hz), 142.90, 125.15, 115.75 (q, J=172.5 Hz), 70.20, 62.60, 52.70, 34.50; HRMS clcd for $C_8H_{11}F_3N_4O_3^+$ m/z $(M+Na)^+$ 291.0664, found 291.0666.

Example 17

Final Step to ET0876 of FIG. 6B

A solution of 14 (26.3 g, 47.6 mmol) in $AcOH/H_2O$ mixture (2:1, 300 mL) was stirred at room temperature for 12 h after which the acid/water mixture stripped at high vacuum. The residue was azeotroped 3 times with 100 mL portions of toluene and then methanol. The resulting residue was dried under high vacuum overnight to obtain ET0876 as transparent glue which solidified into a white wax (22.4 g, 99% yield) upon storage at 2-8° C., and remains solid when left at room temperature). $^1H$ NMR (300 MHz, $CD_3OD$) δ 8.05 (s, 2H), 4.75 (s, 4H), 4.59 (dd, J=14.3, 3.9 Hz, 2H), 4.44 (dd, J=14.3, 8.1 Hz, 2H), 4.13 (m, 2H), 4.03 (t, J=13.8 Hz, 4H), 3.64 (dd, J=11.7, 4.8 Hz, 2H), 3.56 (dd, J=11.7, 6.0 Hz, 2H); $^{19}F$ NMR (282 MHz, $CD_3OD$) δ −121.57; $^{13}C$ NMR (75 MHz, $CD_3OD$) δ 143.00, 126.02, 70.22, 64.31, 62.64, 52.66, 48.84; HRMS clcd for $C_{16}H_{24}F_4N_6O_6^+$ m/z [M+H]+ 473.1753, found 473.1758.

Example 18

Final Step to ET0886 of FIG. 6B

To a solution of 15 (11.1 g, 13.0 mmol) in $AcOH/H_2O$ mixture (8:2, 150 mL) was added 300 µL HCl and the resulting mixture heated at 70° C. for 12 h. The acid/water mixture was stripped in vacuo and the resulting residue azeotroped 3 times with 50 mL portions of toluene. The ensuing residue was diluted with water (100 mL), titrated to pH 3.2 with NaOH and freeze dried to obtain a white solid (8.9 g, 98% yield). Analytical samples were further purified by passing through a short pad of silica gel eluted with 10-40% $MeOH/CH_2Cl_2$ gradient. $^1H$ NMR (300 MHz, $CD_3OD$) δ 8.10 (s, 2H), 5.81 (s, 4H), 5.12 (d, J=3.6 Hz, 1H), 4.96 (s, 4H), 4.52 (d, J=7.8 Hz, 2H), 3.82 (m, 3H), 3.67 (m, 3H), 3.45 (m, 3H), 3.30 (m, 3H); $^{19}F$ NMR (282 MHz, $CD_3OD$) δ −143.39; $^{13}C$ NMR (75 MHz, $CD_3OD$) δ 145.87, 145.77, 123.93, 96.73, 92.62, 85.27, 82.48, 76.40, 74.83, 72.35, 71.58, 69.99, 69.93, 65.31, 65.17, 61.33, 61.21, 40.92; HRMS clcd for $C_{26}H_{32}F_4N_6O_{12}^+$ m/z $[M+H]^+$ 697.2098, found 697.2103.

Example 19

Final Step to ET0890 of FIG. 6B

To a solution of 16 (5.6 g, 5.8 mmol) in $AcOH/H_2O$ mixture (8:2, 100 mL) was added 150 µL HCl and the resulting mixture heated at 70° C. for 12 h. The acid/water mixture was stripped in vacuo and the resulting residue azeotroped 3 times with 50 mL portions of toluene. The ensuing residue was diluted with water (100 mL), titrated to pH 3.2 with NaOH and freeze dried to obtain a white solid (4.4 g, 95% yield). Analytical samples were further purified by passing through a short pad of silica gel eluted with 10-40% $MeOH/CH_2Cl_2$ gradient. $^1H$ NMR (300 MHz, $CD_3OD$) δ 8.05 (s, 2H), 7.83 (s, 1H), 7.71 (s, 2H), 5.13 (d, J=3.3 Hz, 1H), 4.98-4.51 (m, 8H), 3.82 (m, 3H), 3.68 (m, 3H), 3.50-3.22 (m, 7H); $^{19}F$ NMR (282 MHz, $CD_3OD$) δ −62.65; $^{13}C$ NMR (75 MHz, $CD_3OD$) δ 140.69, 131.95 (q, J=33.0 Hz), 127.52, 124.91, 124.28, 121.52, 121.12, 96.75, 92.62, 85.19, 82.32, 82.27, 76.82, 79.39, 74.84, 72.35, 71.55, 70.29, 70.07, 69.98, 65.19, 65.10, 61.38, 61.29, 50.70; HRMS clcd for $C_{30}H_{36}F_6N_6O_{13}^+$ m/z $[M+H]^+$ 805.2456, found 805.2467.

Example 20

Preparation of $^{19}F$ Liposomes

A lipid mixture consisting of 1,2-dipalmitoyl-sn-glycero-3-phosphocholine (DPPC), cholesterol, and 1,2-distearoyl-sn-glycero-3-phosphoethanolamine-N-[methoxy (polyethylene glycol)-2000] (DSPE-mPEG-2000) in a molar ratio of 55:40:5 was used to make liposomes. The lipid mixture, weighed to result in a final lipid concentration of 150 mM was dissolved in 100% ethanol, at a volume of 10% of desired final volume. The solution was then warmed in a water bath, maintained at 60-64° C., to obtain a clear solution. After the lipids had completely dissolved, a pre warmed solution of the desired compound dissolved in histidine/saline buffer (10 mM with no pH adjustment) was added: for ET0863 and ET0876, the concentration of the compound was 1.0 M while for ET0886 and ET0890 the concentrations were 0.8 and 0.5 M respectively. The resulting mixture was incubated at 60-64° C. for 45 min and the spontaneously formed multilamellar liposomes extruded on a Lipex thermoline extruder (Northern Lipids Inc., Canada), beginning with five passes through a 400 nm Nuclepore membrane (Waterman, Newton, Mass.) followed by eight passes through a 100 nm membrane. The resulting preparation was subjected to diafiltration through a 500 kD membrane (Spectrum Labs, Rancho Dominguez, Calif.) for 10 volume exchanges to practically eliminate any unencapsulated compound. Mean particle size was determined by Dynamic Light Scattering on a BI-90 goniometer/autocorrelator system at 90° using a 532 nm solid state laser source (Brookhaven Instruments Corp, Holtville, N.Y.), and the final $^{19}F$ content determined by comparing 19F NMR integrals against a standard solution prepared from analytical grade trifluoroacetic acid (Sigma Aldrich), as previously described [13].

Example 21

MRI Acquisition and Data Processing

A. Procedures

All MRI scans were performed on a 9.4 T Bruker small animal MR scanner equipped with a $^1H/^{19}F$ dual-tunable volume RF coil (35 mm inner diameter, 50 mm length; Rapid Biomed, Würzburg, Germany), located in the Small Animal Imaging Facility (SAIF) at Texas Children's Hospital, Houston, Tex. $^{19}F$ images of both phantoms and mice were acquired with an MMSE scan protocol (Excitation bandwidth=2000 Hz, TR=2000 ms, TE=8.95 ms, scan time=10 min 40 s). $^1H$ images were acquired with a Turbo-RARE T2 scan protocol (TR=2500 ms, TE=11 ms, RARE factor=4, scan time=5 min 20 s). Mice were anethetized by exposure to Isoflurane prior to injection of probes and maintained under anethesia for the duration of the experiment, as well as a temperature of 37° C. using a temperature controlled air-flow system. Dicoms obtained from scans were processed using the OsiriX v.5.8.5 software (Pixmeo SARL, Bernex, Switzerland).

B. Results

Three non-ionic hydrophilic moieties including glycerol, glucose, and triglycerol were employed in the molecular design and 'click' chemistry [14], was used in the key step of the synthesis. Precursors of both the fluorinated and hydrophilic moieties were introduced in this step as either the azido or alkynyl derivative based on the ease and efficiency of preparation from commercially available starting materials as shown in FIGS. 6A-6B. Coupling of the respective hydrophilic and fluorinated moieties followed by deprotection to obtain the final compounds (FIG. 2B) all proceeded with excellent yields, and were optimized to generate gram quantities of each compound. All intermediates and final compounds were characterized by $^1$H and $^{13}$C NMR, HRMS, and $^{19}$F NMR (where applicable).

As shown in FIG. 1 (a) all final products were obtained as solids at room temperature and readily dissolved in aqueous media (water, saline, PBS, and histidine/saline buffers), to give clear solutions, with some at ≥1 M concentrations (b). $^{19}$F NMR of the solutions each gave a single peak: −75.90, −121.57, −143.39 and −62.65 ppm for ET0863, ET0876, ET0886, and ET0890, respectively (c). The single peaks indicate both the magnetic and chemical purity of each compound (estimated overall chemical purity >95%). $^{19}$F MR images of phantoms of these solutions showed no chemical shift artifacts, as expected (d).

The liposome nanoparticle platform for formulation was chosen primarily because of its versatility as a nano vector and its long history of in vivo use. Additionally, liposome surfaces can easily be modified with a variety of ligands and targeting moieties including small molecules and antibodies to bind specific in vivo molecular targets with high efficiency [9]. Formulation of all four compounds using standard protocols as described in the methods section proceeded smoothly. Particle size measured by dynamic light scattering (DLS), showed a mean diameter of 164.76±1.16 nm and a polydispersity of 0.10±0.04. The final $^{19}$F concentrations of ET0876, ET0886, and ET0890 were 22.7±1.4, 21.9±0.3, and 16.6±1.7 mg/mL respectively, reflective of the concentration of individual compounds in the hydration buffer. Preliminary stability testing in plasma at 37° C. showed that ET0863 particles leaked more than 5% of their content within a 1.5 hour test period. ET0876, ET0886, and ET0890 particles all showed less than 5% leak, and were retained for use in subsequent experiments.

Figure 2:
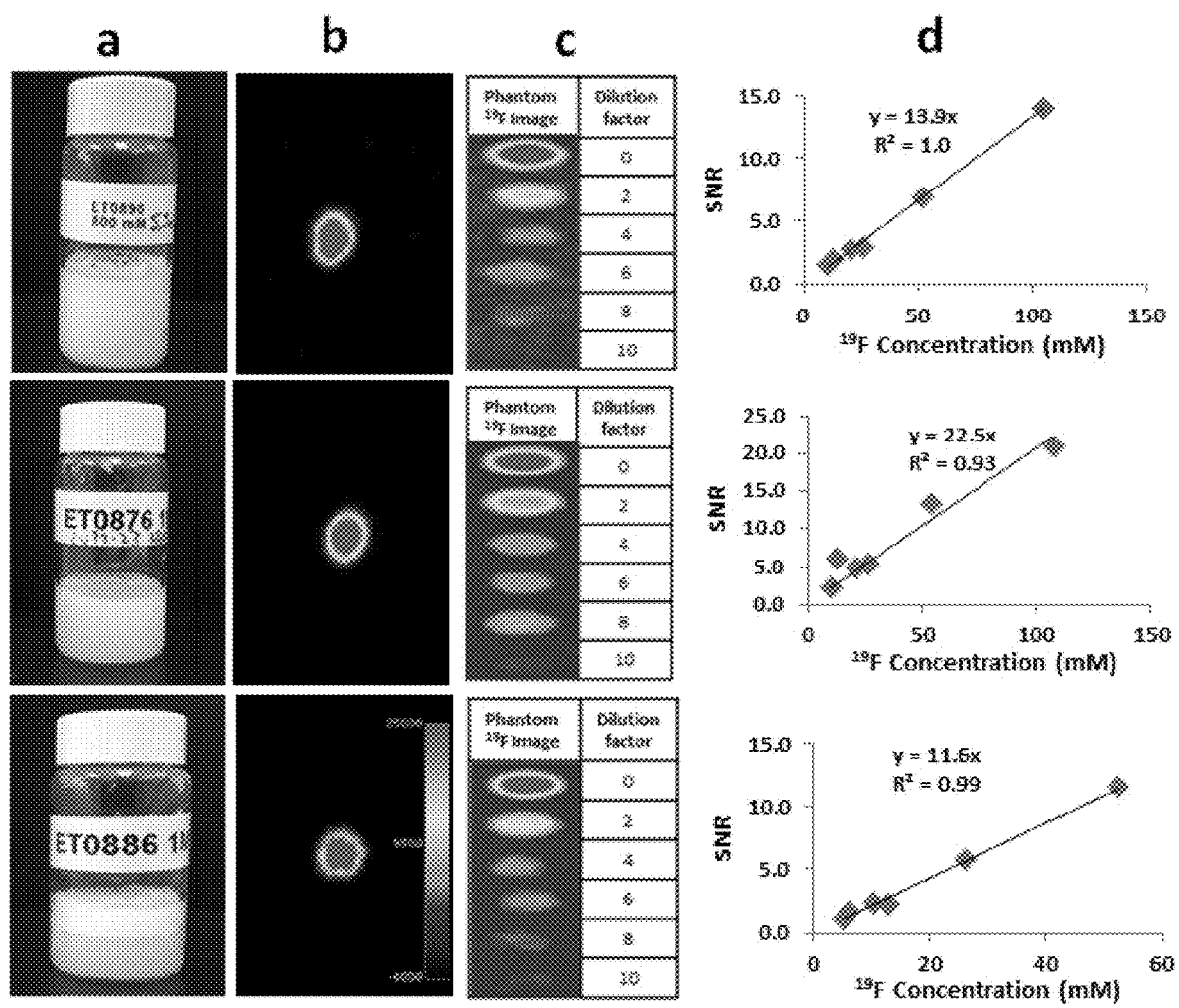
FIG. 2. Select properties and sensitivity of liposome formulations for three compounds (ET0890, ET0876, and ET0886). (a) includes photographs of liposome formulations of the three compounds. (b)[19]F MR image from a 19F MSME (Excitation bandwidth=2000 Hz, TR=2000 ms, TE=8.95 ms, scan time=10 min 40 s) scan of phantoms of the individual formulations. (c) Dilution studies on each formulation demonstrate that a signal can be obtained from each formulation at up to 8-fold dilution. (d) A plot of signal-to-noise (SNR) against concentration shows linear correlation between SNR and concentration.
Figure 3:
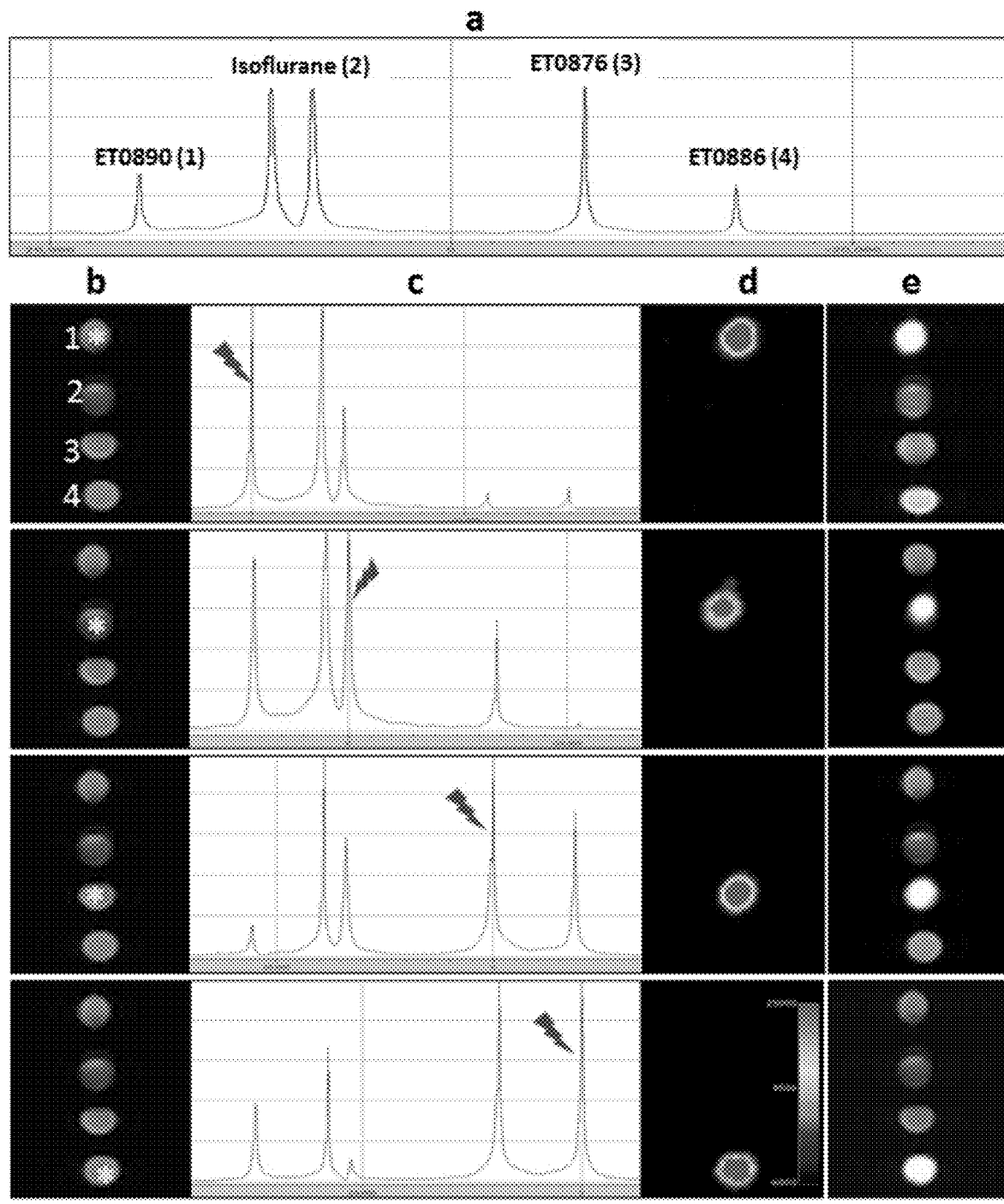
FIG. 3. $^{19}$F MRI of phantoms in the presence of isoflurane demonstrates the utility of liposome formulations of new fluorinated compounds as molecular painting probes. (a) Single pulse $^{19}$F MR scan of a mixture showing resonance frequencies of all fluorine species in the magnet. (b) TurboRARE T2 (TR=2500 ms, TE=11 ms, Rare factor=4, scan time=5 min 20 s, Matrix size=64×64), $^{1}$H MR image of phantoms (1=ET0890, 2=Isoflurane, 3=ET0876, and 4=ET0886). (c) Single pulse $^{19}$F MR scan with resonance frequency of the starred phantom (from (b)) indicated by the lightning-shaped pointer. (d)$^{19}$F MR image following a $^{19}$F MSME scan of the selected frequency. (e) Overlay of $^{19}$F MR image over T2 $^{1}$H MR image of all the phantoms, conveys the exact location of each phantom on the sample rack.

FIG. 2 shows $^{19}$F MRI scans on phantoms of each neat formulation (a), using similar scan parameters as in the solution phantoms (b), gave $^{19}$F signals with SNR of 21.1, 14.0, and 11.6 for ET0876, ET0886, and ET0890 formulations, respectively. Dilution studies (c) showed that each of them was detectable at an 8 fold dilution, and a plot of the SNR against concentration (d) shows a linear relationship between concentration and signal intensity.

To evaluate the potential of these compounds for molecular painting, phantoms of all three formulations were scanned together with a phantom containing Isoflurane (the widely used inhalable fluorinated anesthetic in small animal studies). FIG. 2 shows a single pulse $^{19}$F MR frequency sweep (a), showed peaks corresponding to all the fluorine species in all the phantoms: ET0890 (one peak), Isoflurane (two peaks), ET0876 (one peak), and ET0886 (one peak). An image from a $^1$H MRI scan (b), showed the location of each phantom within the field of view in the coil: ET0890 (position 1), Isoflurane (position 2), ET0876 (position 3), and ET0886 (position 4). When the phantoms were subjected to the same $^{19}$F MSME scan sequence as above, with the highlighted peak position set as the base frequency (c), only the phantom containing that species generated a $^{19}$F MR image (shown in pseudo-color, (d)). An overlay of the $^{19}$F image over the $^1$H T2 image, allowed visualization of the exact location of that signal in the entire field of view (e).

Figure 4:
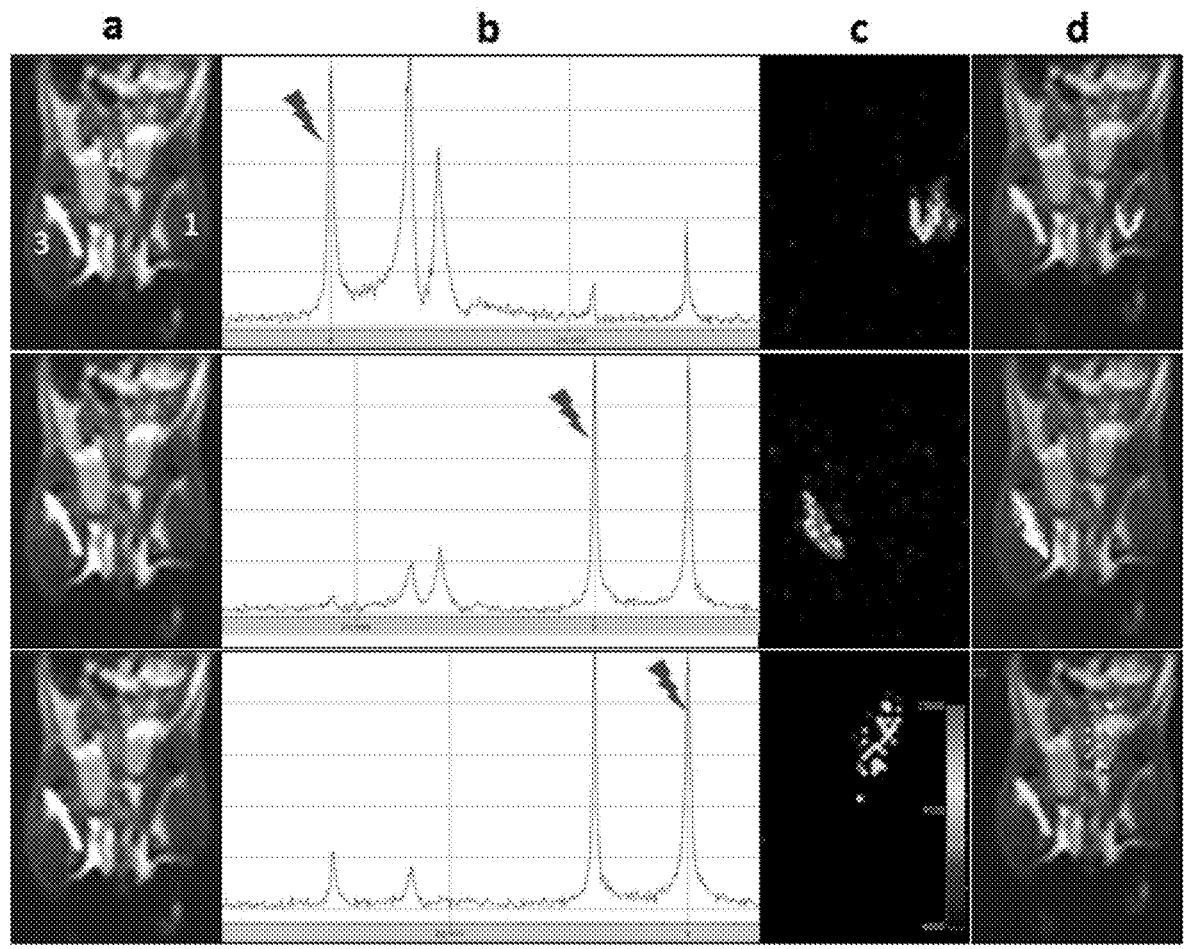
FIG. 4. In vivo evaluation of molecular painting potential of liposomal $^{19}$F MRI probes. (a) TurboRARE $^{1}$H MR anatomy image of a mouse injected intramuscularly with formulations ET0876 (right thigh, position 3), and ET0890 (left thigh, position 1), and subcutaneously with ET0886 (abdomen, position 4), respectively. (b) Single pulse $^{19}$F MR scan showing resonance frequencies of $^{19}$F species within the subject in the scanner with frequencies of interest highlighted by the lightning-shaped pointer. (c)$^{19}$F MR images from $^{19}$F MSME scans of selected frequencies. (d) Overlay of $^{19}$F MR image over anatomy image reports on location of each probe.

Preliminary evaluation of the reproducibility of the in vitro results in an in vivo environment was performed. 50 µL of each formulation were injected as follows: intramuscularly (ET0876 in right thigh and ET0890 in the left thigh), and subcutaneously (ET0886 in the abdominal area), in C57BL6 mice (n=4). As shown in FIG. 4 each animal was anesthetized with isoflurane, placed in the magnet, and imaged using the same scan protocol as the phantoms. First, a TurboRARE T2 $^1$H scan, with the lower torso of the animal in the field of view to show the general anatomy (the numbers 1, 3 and 4 indicate the locations in which the probes were administered, (a)), was performed. When the animal was imaged using the $^{19}$F MSME sequence with the base frequency set to the resonance frequency of highlighted peak on the Single pulse $^{19}$F spectrum (b), only a single $^{19}$F signal, corresponding to that peak was generated on the $^{19}$F MR image (c). Overlay of the $^{19}$F image over the anatomy image showed the exact location of each $^{19}$F spot (d), confirming the ability of the $^{19}$F contrast agents to be used to visualize different targets in parallel. The more diffuse signal in the abdominal area was attributed to faster diffusion of the nanoparticles within the subcutaneous space compared to within the muscle.

Figure 5:
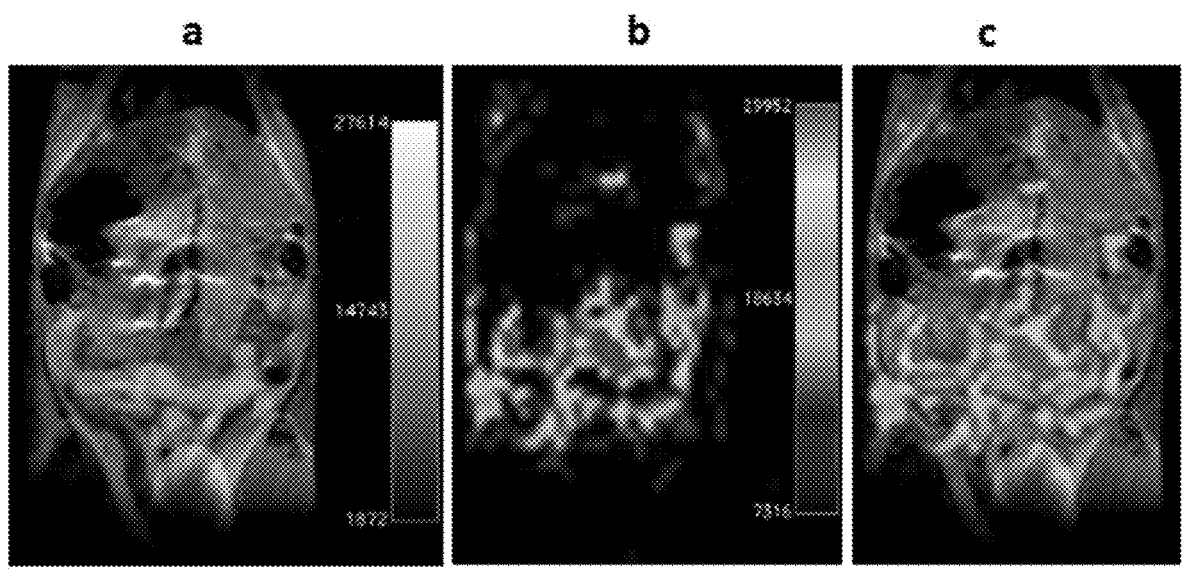
FIG. 5. $^{19}$F MRI of lower torso of mouse under Isoflurane anesthezia. (a) TurboRARE T2 (TR=2500 ms, TE=11 ms, Rare factor=2, scan time=5 min 20 s, Matrix size=256× 256)$^{1}$H MR anatomy image. (b)$^{19}$F MR image from a $^{19}$F TurboRARE T2 scan (TR=875 ms, TE=11 ms, Rare factor=5, scan time=56 min 42 s, Matrix size=64×64), show very strong signal from the fluorinated anesthesia. (c) Overlay of $^{19}$F MR image over anatomy shows uptake of the anesthesia in belly fat.

To demonstrate the significance of the non-interference of the isoflurane signal with the signal from these probes, mice anesthetized with isoflurane were imaged with a scan sequence optimized for studies with one of the most popular PFPEs currently in use. As shown in FIG. 5, the anesthesia generates a very strong in vivo $^{19}$F MRI signal attributed to the high lipophilicity of the gas.

Example 22

Figure 7A:
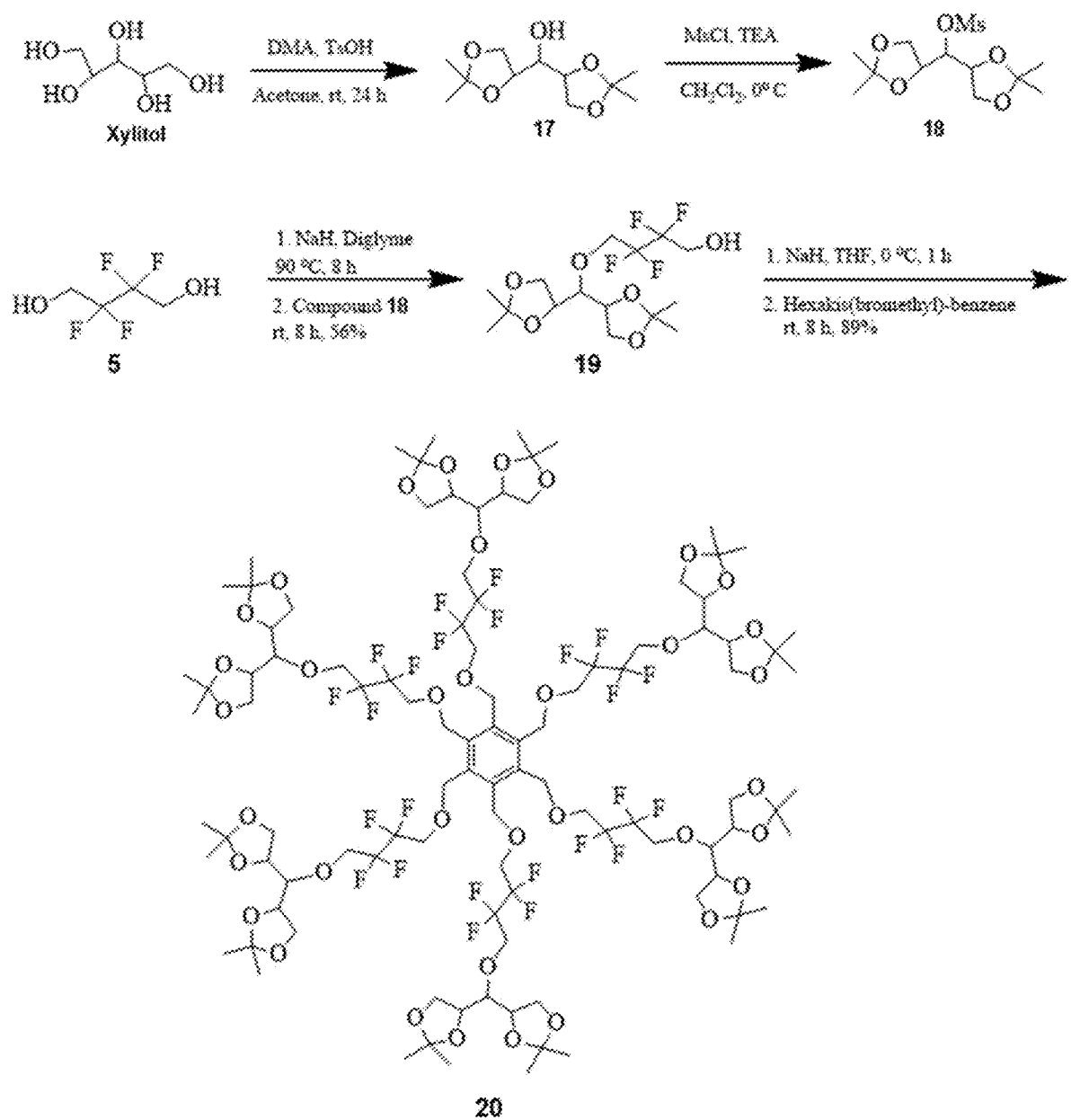
FIGS. 7A-7B depict a synthetic scheme for compound ET1084.
Figure 7B:
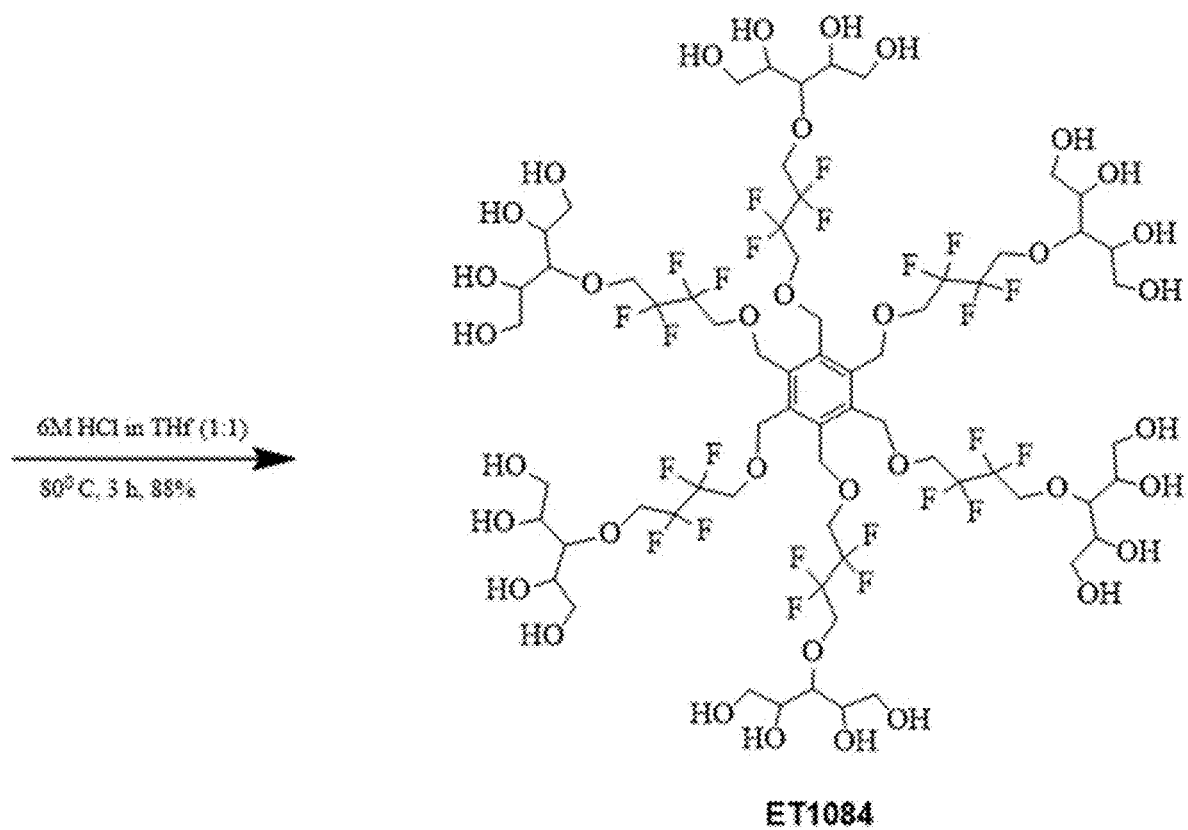

Synthesis of ET1084 of FIG. 7B

Compound 17 of FIG. 7A: Methanol (100 mL), dimethoxy acetone (60.0 mL), and acetone (2000 mL) were added to xylitol (50.0 g, 329 mmol) in a conical flask at ambient temperature. To the resultant mixture, tosic acid (5.65 g, 32.8 mmol) was added, followed by vigorous stirring until all solids were dissolved. The reaction mixture was then allowed to stir at room temperature overnight, followed by addition of K$_2$CO$_3$ (4.54 g, 32.8 mmol). The ensuing mixture was stirred for 30 min., followed by filtration of all solids. The filtrate was concentrated in-vacuo. The resultant colorless oil was purified by column chromatography eluted with 40% ethylacetate/pentane through a short pad of silica yielding the alcohol 17 (64.8 g, 279 mmol, 85%) as a colorless oil. $^1$H NMR (600 MHz; CDCl$_3$): δ 4.18-4.15 (m, 1H), 4.02 (t, J=6.9 Hz, 2H), 3.95-3.93 (m, 1H), 3.83 (t, J=7.7 Hz, 1H), 3.77 (dd, J=12.0, 1.7 Hz, 1H), 3.61 (dd, J=12.0, 4.3 Hz, 1H), 1.38 (d, J=30.6 Hz, 12H). $^{13}$C NMR (151 MHz; CDCl$_3$): δ 109.7, 109.6, 77.7, 75.1, 65.9, 65.6, 62.1, 27.1, 26.9, 26.1, 25.4.

Compound 18 of FIG. 7A: To a solution of the alcohol 17 (50.0 g, 215 mmol) in CH$_2$Cl$_2$ (1000 mL) was added trimethylamine (90.0 mL, 646 mmol), and the resultant solution was cooled to 0° C. for 30 min. Mesylchloride (21.7 mL, 280 mmol) was added, and the reaction mixture was allowed to warm to room temperature over 1 h. This was then poured into saturated ammonium chloride solution (500 mL) in a separatory funnel. The organic phase was separated and the aqueous phase was extracted twice with CH$_2$Cl$_2$. The organic phases were combined and dried over anhydrous Na$_2$SO$_4$, filtered and concentrated to obtain a brown paste which was recrystallized in diethylether to obtain mesylate 18 (41.9 g, 135 mmol, 63%) as pale white crystalline flakes. $^1$H NMR (600 MHz; CDCl$_3$): δ 4.43 (dd, J=11.2, 3.0 Hz, 1H), 4.30 (dd, J=11.2, 5.3 Hz, 1H), 4.28-4.24 (m, 2H), 4.10 (t, J=7.7 Hz, 1H), 4.01 (dd, J=8.1, 3.9 Hz, 1H), 3.93 (t, J=7.6 Hz, 1H), 3.10 (s, 3H), 1.46-1.39 (m, 12H). $^{13}$C NMR (151 MHz; CDCl$_3$): δ 110.4, 109.9, 76.5, 74.9, 74.2, 68.8, 65.4, 37.7, 26.95, 26.91, 26.0, 25.2.

Compound 19 of FIG. 7A: Alcohol 5 (FIG. 6A) (25.0 g, 154 mmol) was added slowly to a suspension of NaH powder (12.3 g, 308 mmol, 60% in mineral oil) in dry diglyme (1 L) at 0° C. The mixture was stirred for 1 h followed by addition of mesylate 18 (19.2 g, 61.7 mmol). The ice/water bath was replaced with an oil bath and heated at 90° C. for 8 hours. The resultant dark solution was carefully poured into ice/water solution followed by removal of volatiles by rotary evaporation under high vacuum. The resulting brown solid was purified using flash column chromatography (10-55% ethyl acetate/hexanes gradient) yielding alcohol 19 (13.0 g, 34.6 mmol, 56%) as a colorless oil. $^1$H NMR (600 MHz; CDCl$_3$): δ 4.21 (q, J=5.7 Hz, 1H), 4.14 (dt, J=8.3, 4.2 Hz, 1H), 4.06 (q, J=7.3 Hz, 1H), 4.01 (qd, J=13.5, 6.8 Hz, 4H), 3.94 (dd, J=8.1, 4.2 Hz, 1H), 3.90 (t, J=7.7 Hz, 1H), 3.82 (dd, J=10.4, 3.5 Hz, 1H), 3.73 (dd, J=10.4, 5.4 Hz, 1H), 3.02 (t, J=7.6 Hz, 1H), 1.44-1.39 (m, 12H). $^{13}$C NMR (151 MHz; CDCl$_3$): δ 110.1, 109.8, 77.2, 76.0, 74.8, 72.6, 68.3 (t, J=28.19), 65.5, 60.5 (t, J=28.21), 26.9, 26.1, 25.3.

Compound 20 of FIG. 7A: To a suspension of NaH powder (2.17 g, 55.2 mmol, 60% in mineral oil) in dry THF (200 mL) at 0° C. was added alcohol 19 (9.50 g, 25.2 mmol) and stirred at 0° C. for an addition 1 h. To this was added hexakis(bromomethylbenzene) (2.47 g, 3.88 mmol), and the ensuing mixture was stirred at room temperature for 12 h. This was carefully poured into ice/water mixture and concentrated by rotary evaporation under reduced pressure. The resulting brown solid was purified using flash column chromatography (15-60% ethyl acetate/hexanes gradient) to yield compound 20 (8.35 g, 3.47 mmol, 89%) as a pale yellow thick syrup. $^1$H NMR (600 MHz; CDCl$_3$): δ 4.85 (s, 12H), 4.19 (q, J=5.8 Hz, 6H), 4.10 (dt, J=8.1, 4.2 Hz, 6H), 4.02 (m, 30H), 3.95 (dd, J=7.9, 4.6 Hz, 6H), 3.86 (t, J=7.8 Hz, 6H), 3.78-3.71 (m, 12H), 1.44-1.39 (m, 72H). $^{13}$C NMR (151 MHz; CDCl$_3$): δ 137.7, 109.9, 109.7, 77.7, 76.4, 75.2, 72.8, 68.2, 68.0, 67.8, 65.6, 26.9, 26.2, 25.4. $^{19}$F NMR (282 MHz; CDCl$_3$): δ -121.1, -121.3.

Final step to ET1084 of FIG. 7B: A THF/6M HCl mixture (1:1, 100 mL) was added to compound 20 (6.80 g, 2.80 mmol), and the resulting solution was refluxed at 80° C. for 3 h. This was followed by evaporation of the solvents and dilution of the residue with water (20.0 mL). The resulting acidic solution was neutralized by adding NaOH solution (2 M) dropwise. The resulting mixture was freeze dried to obtain a white solid which was redissolved in ethanol and filtered to remove inorganic salts. The ethanol from the filtrate was removed by rotary evaporation and residue was redissolved in water and freeze dried to obtain compound ET1084 (4.75 g, 2.47 mmol, 88%) as a white solid. $^1$H NMR (600 MHz; MeOD): δ 4.94 (s, 12H), 4.11 (t, J=14.9 Hz, 12H), 4.00 (t, J=14.3 Hz, 12H), 3.90 (d, J=4.2 Hz, 6H), 3.75 (dd, J=9.4, 4.3 Hz, 12H), 3.68 (dt, J=10.9, 5.6 Hz, 12H), 3.63 (t, J=4.8 Hz, 12H). $^{13}$C NMR (151 MHz; MeOD): 137.7, 73.9, 42.4, 70.9, 70.6, 67.8 (t, 25 Hz) 67.2 (t, 24.9 Hz), 62.9, 61.4. $^{19}$F NMR (282 MHz; MeOD): δ -122.7, -123.0. HRMS: Calculated for C$_{66}$H$_{102}$F$_{24}$O$_{36}$Na$^+$ is 1949.57, experimental 1949.56.

Example 22

$^{19}$F-MR Phantom Images Using ET1084

Figure 9:
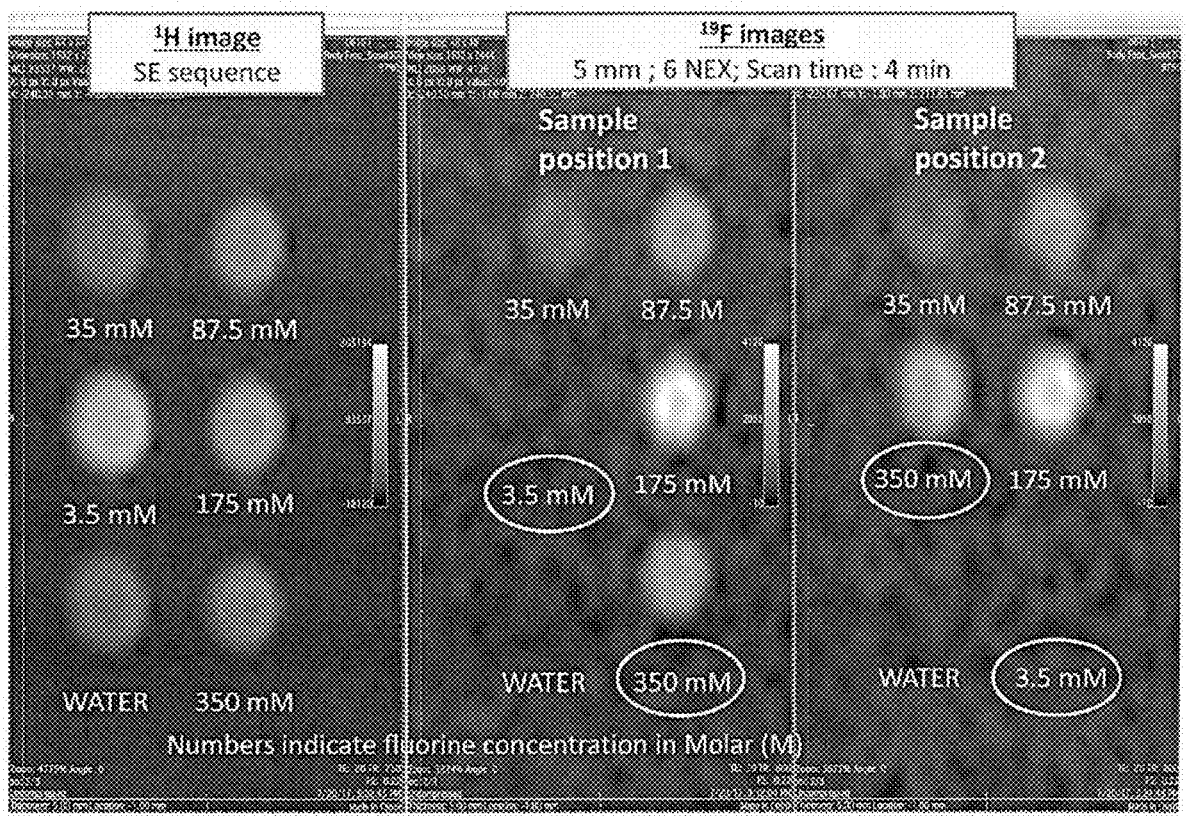
FIG. 9. $^{19}$F MRI of phantoms of an aqueous solution of $^{19}$F MR contrast molecule ET1084 at the indicated concentrations. $^{1}$H MRI images are also shown (left panel).
Figure 10:
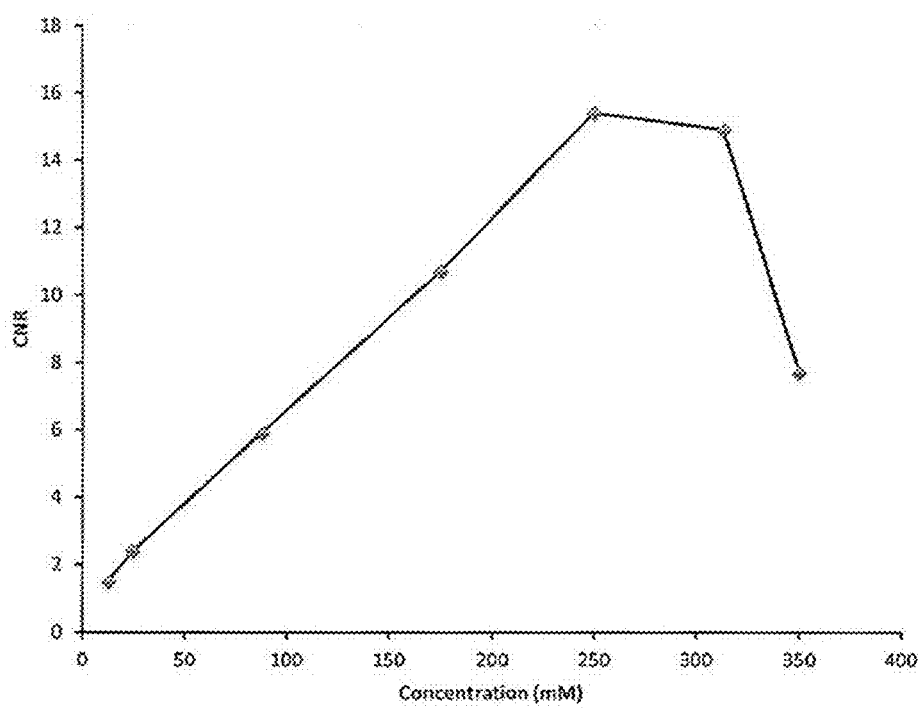
FIG. 10 shows a graph of contrast-to-noise ratio (CNR) for the indicated concentrations of ET1084 in $^{19}$F MRI scans.
Figure 11:
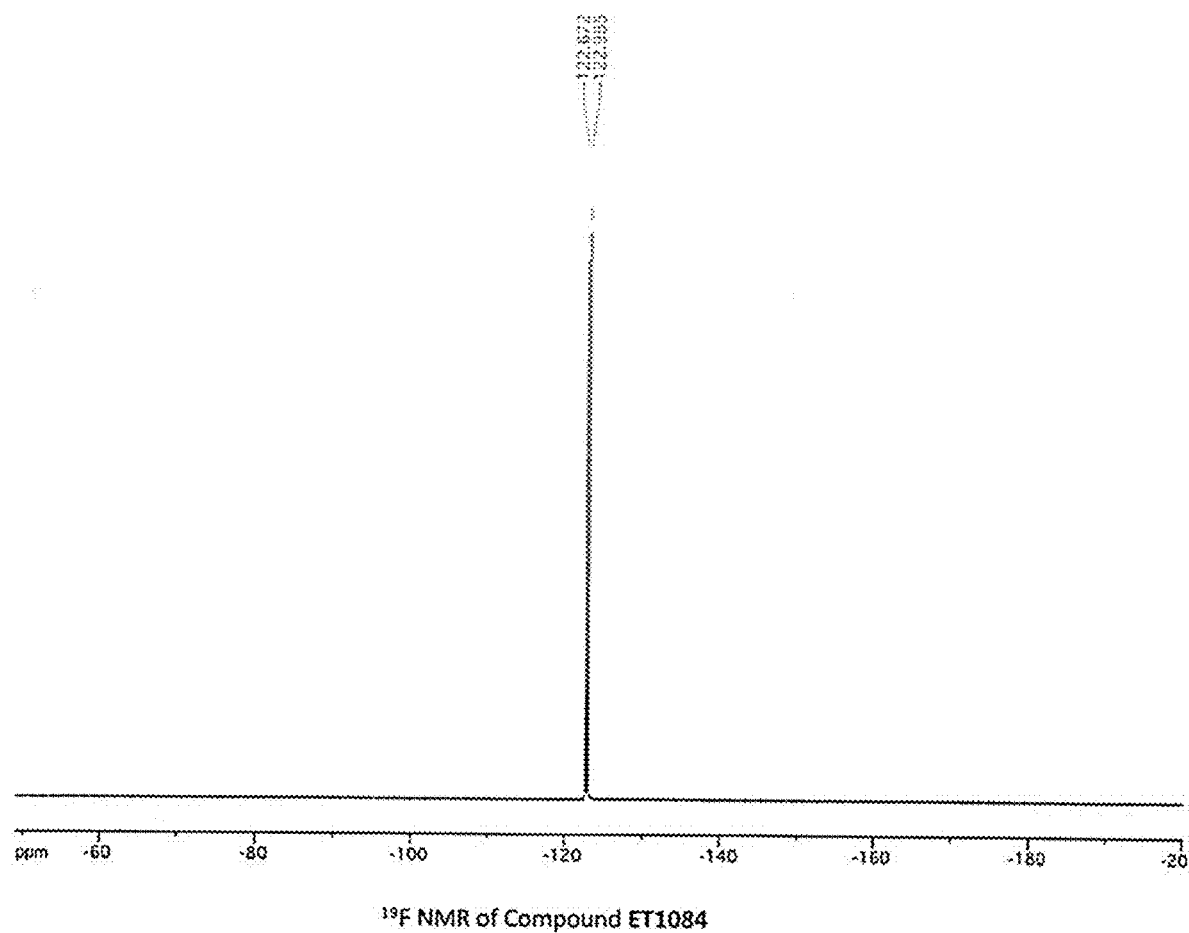
FIG. 11 shows a $^{19}$F NMR spectrum of ET1084.

$^{19}$F MRI phantom images were generated by scanning 300 µl of an aqueous solution of ET1084 at the indicated concentrations using a $^{19}$F spin echo scan protocol in a 1 Tesla instrument. Phantom images shown in FIG. 9 illustrate that ET1084 gives a concentration-dependent signal in a $^{19}$F MRI imaging experiment. A graph of contrast-to-noise ratio (CNR) for various concentrations of ET1084 in $^{19}$F MRI scans is shown in FIG. 10, and a $^{19}$F NMR spectrum of ET1084 is shown in FIG. 11.

REFERENCES

1. Pacanowski M, Huang S M. Precision Medicine. Clinical Pharmacology & Therapeutics. 2016; 99:124.
2. Harris T J R, McCormick F. The molecular pathology of cancer. Nat Rev Clin Oncol. 2010; 7:251-265.
3. Lu Y-F, Goldstein D B, Angrist M, Cavalleri G. Personalized medicine and human genetic diversity. Cold Spring Harb Perspect Med. 2014; 4:a008581.
4. Achilefu S. Introduction to Concepts and Strategies for Molecular Imaging. Chemical Reviews. 2010; 110:2575.
5. Joshi A D, Pontecorvo M J, Adler L, Stabin M G, Skovronsky D M, Carpenter A P, et al. Radiation dosimetry of florbetapir F 18. EJNMMI Research. 2014; 4:4.
6. Debbage P, Jaschke W. Molecular imaging with nanoparticles: giant roles for dwarf actors. Histochemistry and cell biology. 2008; 130:845-875.
7. Allen T M, Cullis P R. Liposomal drug delivery systems: from concept to clinical applications. Advanced Drug Delivery Reviews. 2013; 65:36-48.
8. Srinivas M, Heerschap A, Ahrens E T, Figdor C G, de Vries I J M. (19)F MRI for quantitative in vivo cell tracking. Trends in Biotechnology [Internet]. 2010; 28:363-70. Available from: http://dx.doi.org/10.1016/j.tibtech.2010.04.002
9. Chen J, Lanza G M, Wickline S A. Quantitative Magnetic Resonance Fluorine Imaging: Today and tomorrow. Wiley Interdisciplinary Reviews: Nanomedicine and Nanobiotechnology [Internet]. 2010; 2:431. Available from: http://dx.doi.org/10.1002/wnan.87
10. tirotta I, Dichiarante V, Pigliacelli C, Cavallo G, Terraneo G, Bombelli F B, et al. 19F Magnetic Resonance Imaging (MRI): From Design of Materials to Clinical Applications. Chemical Reviews. 2015; 115:1106.
11. Ruiz-Cabello J, Barnett B P, Bottomley P A. Fluorine (19F) MRS and MRI in biomedicine. NMR in Biomedicine. 2011; 24:114.
12. Wolters M, Mohades S G, Hackeng T M, Post M J, Kooi M E, Backes W H. Clinical Perspectives of Hybrid Proton-Fluorine Magnetic Resonance Imaging and Spectroscopy. Investigative Radiology. 2013; 48:341.
13. Srinivas M, Morel P A, Ernst L A. Fluorine-19 MRI for visualization and quantification of cell migration in a diabetes model. Magnetic. 2007; 58:725-734.
14. Kolb H C, Finn M G, Sharpless K B. Click Chemistry: Diverse Chemical Function from a Few Good Reactions. Angewandte Chemie International Edition. 2001; 40:2004.
15. Marusyk A, Polyak K. Tumor heterogeneity: Causes and consequences. Biochimica et Biophysica Acta (BBA)—Reviews on Cancer. 2010; 1805:105.

16. Almendro V, Marusyk A, Polyak K. Cellular Heterogeneity and Molecular Evolution in Cancer. Annual Review of Pathology: Mechanisms of Disease. 2013; 8:277.

17. Jeraj R, Bradshaw T, Simoncic U. Molecular Imaging to Plan Radiotherapy and Evaluate Its Efficacy. J Nucl Med. 2015; 56:1752-1765.

18. Bentzen S M, Gregoire V. Molecular imaging-based dose painting: A novel paradigm for radiation therapy prescription. Semin Radiat Oncol. 2011; 21:101-110.

19. Partlow K C, Chen J, Brant J A, Neubauer A M. 19F magnetic resonance imaging for stem/progenitor cell tracking with multiple unique perfluorocarbon nanobeacons. The FASEB Journal. 2007; 21:1647-1654.

20. Matsuoka K. Micellization of fluorinated amphiphiles. Current Opinion in Colloid & Interface Science. 2003; 8:227.

21. Kimura A, Narazaki M, Kanazawa Y, Fujiwara H. 19F Magnetic resonance imaging of perfluorooctanoic acid encapsulated in liposome for biodistribution measurement. Magnetic Resonance Imaging. 2004; 22:855.

22. Langereis S, Keupp J, van Velthoven J L J, de Roos I H C, Burdinski D, Pikkemaat J A, et al. A Temperature-Sensitive Liposomal 1H CEST and 19F Contrast Agent for MR Image-Guided Drug Delivery. J Am Chem Soc. 2009; 131:1380.

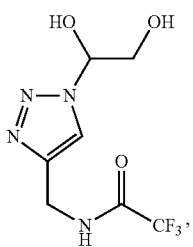
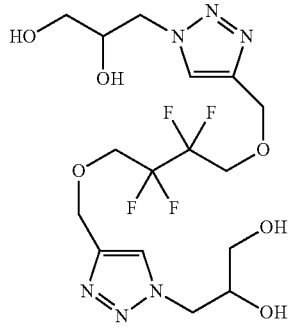
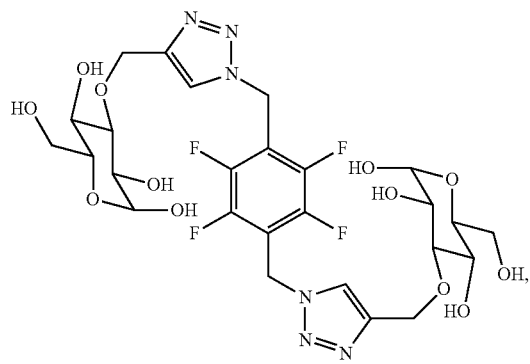
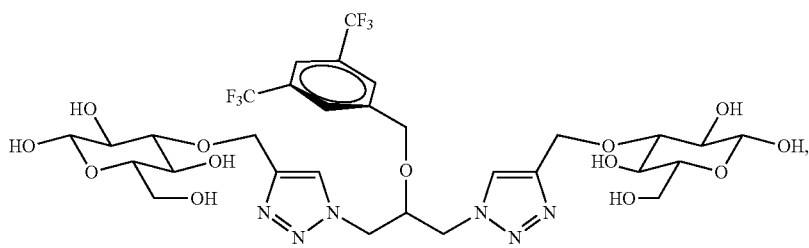
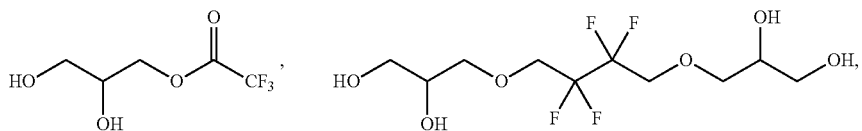

-continued
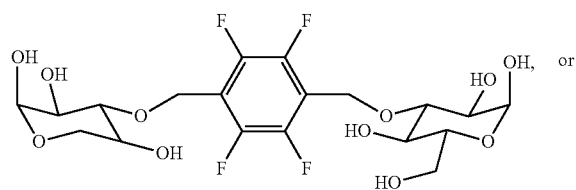 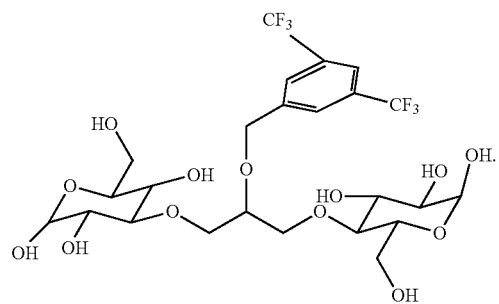

The invention claimed is:

1. A nonionic $^{19}$F-MR contrast dendrimer molecule having the formula X—R$_n$, wherein X is

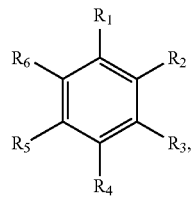

wherein R$_1$-R$_6$ are each independently H or —(CH$_2$O)$_a$(CH$_2$)$_b$(CF$_2$)$_c$(CH$_2$)$_d$—, at least one of R$_1$-R$_6$ is —(CH$_2$O)$_a$(CH$_2$)$_b$(CF$_2$)$_c$(CH$_2$)$_d$—, a, b, and d are each independently an integer from 0 to 5, and c is an integer from 2 to 5, and R is

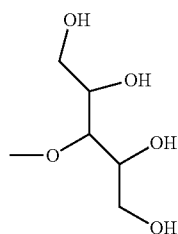

wherein n is an integer equal to or greater than 1, and wherein the molecule has at least one axis of symmetry.

2. The nonionic $^{19}$F-MR contrast molecule of claim 1, wherein the molecule has the structure:

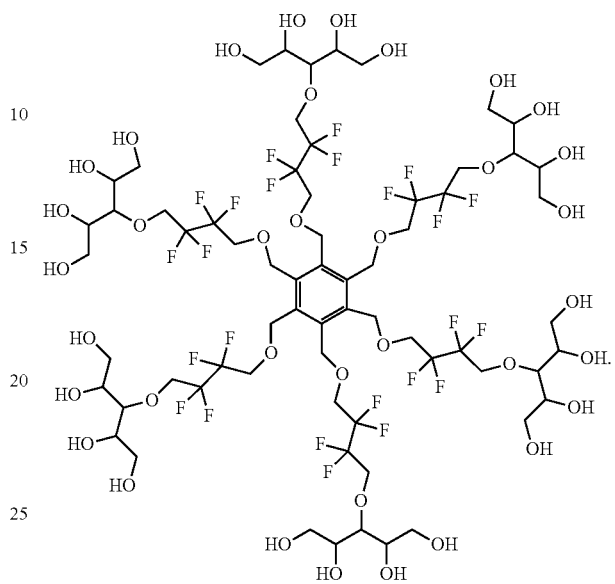

3. A liposome composition for the administration of two or more $^{19}$F-MR contrast molecules, the liposome composition comprising: a liposome and two or more $^{19}$F-MR contrast molecules with unique $^{19}$F-MR signals, wherein each of the two or more $^{19}$F-MR contrast molecules have the formula X—R$_n$, wherein X comprises at least two magnetically equivalent fluorine atoms, wherein the two or more molecules each have at least one axis of symmetry, wherein R is a nonionic, hydrophilic moiety comprising at least one terminal vicinal diol moiety, wherein n is an integer equal to or greater than 1, wherein the two or more $^{19}$F-MR contrast molecules comprise at least a first $^{19}$F-MR contrast molecule and a second $^{19}$F-MR contrast molecule, and wherein the first $^{19}$F-MR contrast molecule has a $^{19}$F-MR signal that is different from the second $^{19}$F-MR contrast molecule and from any other $^{19}$F-MR contrast molecule present in the liposome composition, if any, and wherein for the first $^{19}$F-MR contrast molecule, X is

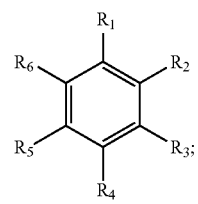

wherein $R_1$-$R_6$ are each independently H or —$(CH_2O)_a$$(CH_2)_b(CF_2)_c(CH_2)_d$—;

at least one of $R_1$-$R_6$ is —$(CH_2O)_a(CH_2)_b(CF_2)_c(CH_2)_d$—;

a, b, and d are each independently an integer from 0 to 5; and c is an integer from 2 to 5;

n is an integer equal to or greater than 1; and

R is

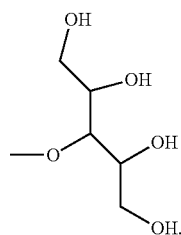

4. The liposome composition of claim 3, wherein for the first $^{19}$F-MR contrast molecule:

the molecule has a C Log P value of less than −1; and the molecule has a topological polar surface area of at least 80.

5. The liposome composition of claim 3, wherein the first $^{19}$F-MR contrast molecule has the structure:

6. The liposome composition of claim 3, wherein for the second $^{19}$F-MR contrast molecule, X is selected from

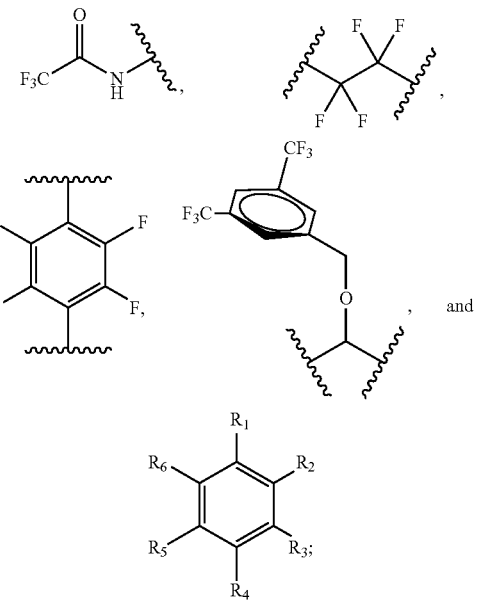

wherein $R_1$-$R_6$ are each independently H or —$(CH_2O)_a$$(CH_2)_b(CF_2)_c(CH_2)_d$—;

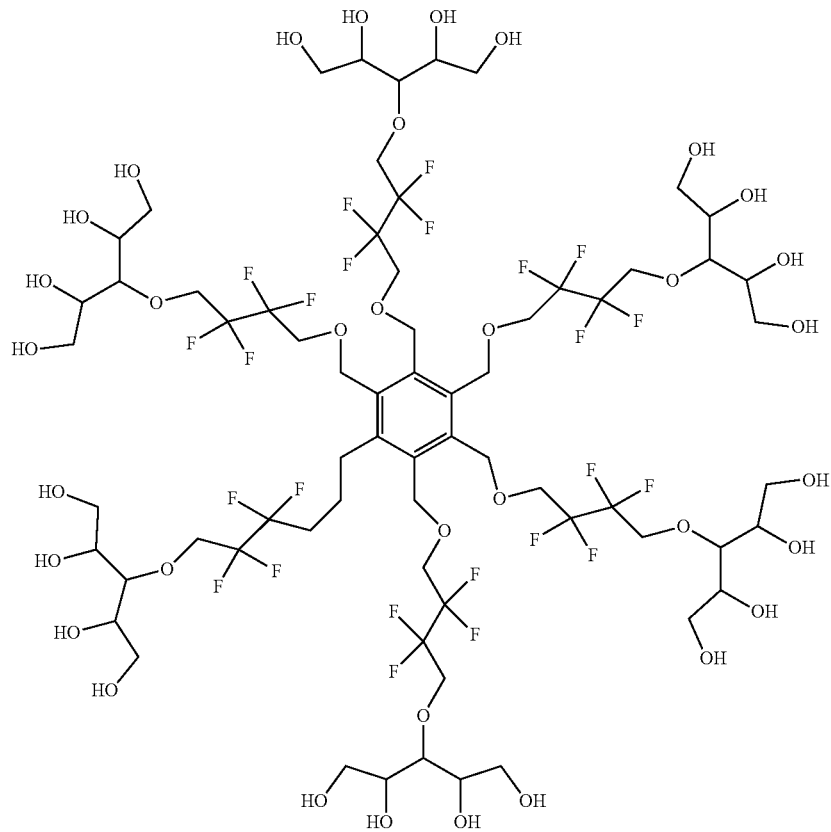 [SMILES: OCC(O)C(OCC(F)(F)C(F)(F)CCCc1c(COCC(F)(F)C(F)(F)COC(C(O)CO)C(O)CO)c(COCC(F)(F)C(F)(F)COC(C(O)CO)C(O)CO)c(COCC(F)(F)C(F)(F)COC(C(O)CO)C(O)CO)c(COCC(F)(F)C(F)(F)COC(C(O)CO)C(O)CO)c1COCC(F)(F)C(F)(F)COC(C(O)CO)C(O)CO)C(O)CO]

at least one of $R_1$-$R_6$ is —$(CH_2O)_a(CH_2)_b(CF_2)_c(CH_2)_d$—;

a, b, and d are each independently an integer from 0 to 5; and c is an integer from 2 to 5.

7. The liposome composition of claim 6, wherein for the second $^{19}$F-MR contrast molecule:

n is 1, 2, 3, 4, 5, or 6;

R comprises a vicinal diol moiety; and the molecule has at least one plane of symmetry and at least one axis of symmetry.

8. The liposome composition of claim 6, wherein for the second $^{19}$F-MR contrast molecule:

the molecule has a C Log P value of less than −1; and the molecule has a topological polar surface area of at least 80.

9. The liposome composition of claim 6, wherein for the second $^{19}$F-MR contrast molecule, R is selected from the group consisting of

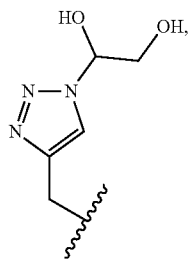
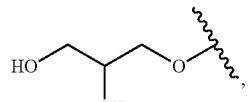
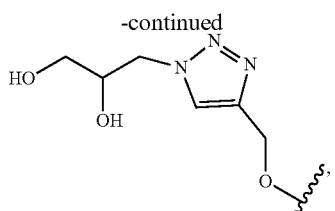
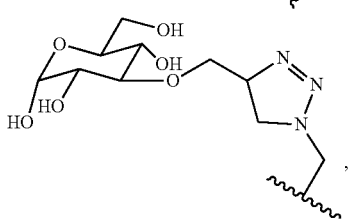
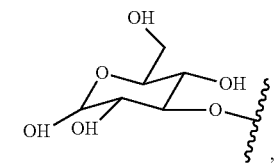
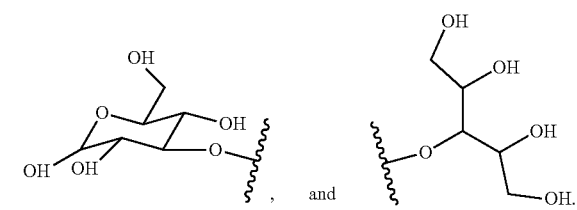

, and

10. The liposome composition of claim 6, wherein the second $^{19}$F-MR contrast molecule has one of the following structures: